United States Patent
Vollmers et al.

(10) Patent No.: US 11,833,343 B2
(45) Date of Patent: *Dec. 5, 2023

(54) DIFFUSION AND INFUSION RESISTANT IMPLANTABLE DEVICES FOR REDUCING PULSATILE PRESSURE

(71) Applicant: Aria CV, Inc., St. Paul, MN (US)

(72) Inventors: Karl Vollmers, Minneapolis, MN (US); Lynn Zwiers, Lino Lakes, CA (US); John Gainor, Mendota Heights, MN (US); John Scandurra, Saint Paul, MN (US)

(73) Assignee: Aria CV, Inc., St. Paul, MN (US)

( * ) Notice: Subject to any disclaimer, the term of this patent is extended or adjusted under 35 U.S.C. 154(b) by 133 days.

This patent is subject to a terminal disclaimer.

(21) Appl. No.: 17/496,719

(22) Filed: Oct. 7, 2021

(65) Prior Publication Data

US 2022/0023614 A1 Jan. 27, 2022

Related U.S. Application Data

(63) Continuation of application No. 17/011,870, filed on Sep. 3, 2020, now Pat. No. 11,141,581.

(Continued)

(51) Int. Cl.
*A61M 60/869* (2021.01)
*A61M 60/268* (2021.01)
(Continued)

(52) U.S. Cl.
CPC ..... *A61M 60/869* (2021.01); *A61B 17/12022* (2013.01); *A61B 17/12027* (2013.01);
(Continued)

(58) Field of Classification Search
CPC .. A61M 60/869; A61M 29/02; A61M 60/268; A61M 60/135; A61M 60/122;
(Continued)

(56) References Cited

U.S. PATENT DOCUMENTS 3,275,001 A 9/1966 Rosecrans
3,634,924 A 1/1972 Blake et al.
(Continued)

FOREIGN PATENT DOCUMENTS

CN 102657910 A 9/2012
CN 103260547 A 8/2013
(Continued)

OTHER PUBLICATIONS

U.S. Appl. No. 13/701,721, U.S. Pat. No. 9,987,153, filed May 31, 2011 / Jun. 5, 2018.
(Continued)

*Primary Examiner* — Diane D Yabut
*Assistant Examiner* — Christina C Lauer
(74) *Attorney, Agent, or Firm* — Evershed Sutherland (US) LLP; Christopher C. Bolten; Albert K. Heng

(57) ABSTRACT

Diffusion and infusion resistant implantable devices and methods for reducing pulsatile pressure are provided. The implantable device includes a balloon implantable within a blood vessel of a patient, e.g., the pulmonary artery. The balloon is injected with a fluid mixture comprising a constituent fluid(s) and a diffusion-resistant gas to provide optimal balloon volume and limit fluid diffusion throughout multiple cardiac cycles. The fluid mixture may be pressurized such that the balloon is transitionable between an expanded state and a collapsed state responsive to pressure fluctuations in the blood vessel.

20 Claims, 13 Drawing Sheets

Related U.S. Application Data

(60) Provisional application No. 62/897,166, filed on Sep. 6, 2019.

(51) Int. Cl.
*A61M 60/122* (2021.01)
*A61M 60/135* (2021.01)
*A61M 60/00* (2021.01)
*A61M 60/274* (2021.01)
*A61B 17/12* (2006.01)
*A61M 1/00* (2006.01)
*A61M 29/02* (2006.01)
*C01B 17/00* (2006.01)
*C01B 17/45* (2006.01)
*A61B 17/00* (2006.01)

(52) U.S. Cl.
CPC .. *A61B 17/12036* (2013.01); *A61B 17/12109* (2013.01); *A61B 17/12131* (2013.01); *A61B 17/12136* (2013.01); *A61M 1/00* (2013.01); *A61M 29/02* (2013.01); *A61M 60/00* (2021.01); *A61M 60/122* (2021.01); *A61M 60/135* (2021.01); *A61M 60/268* (2021.01); *A61M 60/274* (2021.01); *C01B 17/00* (2013.01); *C01B 17/45* (2013.01); *C01B 17/453* (2013.01); *C01B 17/4507* (2013.01); *C01B 17/4515* (2013.01); *A61B 2017/00535* (2013.01); *A61B 2017/00557* (2013.01); *A61M 2202/025* (2013.01); *A61M 2202/0208* (2013.01); *A61M 2202/0225* (2013.01); *A61M 2202/04* (2013.01)

(58) Field of Classification Search
CPC ............... A61M 60/00; A61M 60/274; A61B 17/12136; A61B 17/12131; A61B 17/12109; C01B 17/453; C01B 17/45
See application file for complete search history.

(56) References Cited

U.S. PATENT DOCUMENTS

| | | | |
|---|---|---|---|
| 3,818,903 A | 6/1974 | Bleecker | |
| 4,422,447 A | 12/1983 | Schiff | |
| 4,793,351 A | 12/1988 | Landman et al. | |
| 4,902,273 A | 2/1990 | Choy et al. | |
| 4,938,766 A | 7/1990 | Jarvik | |
| 4,955,905 A | 9/1990 | Reed | |
| 5,002,531 A | 3/1991 | Bonzel | |
| 5,112,303 A | 5/1992 | Pudenz et al. | |
| 5,222,980 A | 6/1993 | Gealow | |
| 5,409,444 A | 4/1995 | Kensey et al. | |
| 5,486,192 A | 1/1996 | Walinsky et al. | |
| 5,496,311 A | 3/1996 | Abele et al. | |
| 5,578,085 A * | 11/1996 | Johnson, Jr. .......... | A61F 2/0063 623/8 |
| 5,713,867 A | 2/1998 | Morris | |
| 5,769,821 A | 6/1998 | Abrahamson et al. | |
| 5,795,325 A | 8/1998 | Valley et al. | |
| 5,814,016 A | 9/1998 | Valley et al. | |
| 5,820,542 A | 10/1998 | Dobak, III et al. | |
| 5,833,655 A | 11/1998 | Freed et al. | |
| 6,017,324 A | 1/2000 | Tu et al. | |
| 6,030,336 A | 2/2000 | Franchi | |
| 6,053,891 A | 4/2000 | DeCampli | |
| 6,136,025 A | 10/2000 | Barbut et al. | |
| 6,210,318 B1 | 4/2001 | Lederman | |
| 6,261,304 B1 | 7/2001 | Hall et al. | |
| 6,461,367 B1 | 10/2002 | Kirsch et al. | |
| 6,558,349 B1 | 5/2003 | Kirkman | |
| 6,559,349 B1 | 5/2003 | Slaugh et al. | |
| 6,576,007 B2 | 6/2003 | Dehdashtian et al. | |
| 6,579,224 B1 | 6/2003 | Burton et al. | |
| 6,682,473 B1 | 1/2004 | Matsuura et al. | |
| 7,044,967 B1 | 5/2006 | Solem et al. | |
| 7,074,178 B2 | 7/2006 | Connors et al. | |
| 7,468,050 B1 | 12/2008 | Kantrowitz | |
| 7,540,876 B2 | 6/2009 | Connors et al. | |
| 7,766,814 B2 | 8/2010 | Walsh | |
| 7,811,249 B2 | 10/2010 | Saab | |
| 7,928,367 B2 | 4/2011 | Hirota et al. | |
| 8,016,740 B2 | 9/2011 | Connors et al. | |
| 8,092,521 B2 | 1/2012 | Figulla et al. | |
| 8,116,883 B2 | 2/2012 | Williams et al. | |
| 8,206,378 B1 | 6/2012 | Kalpin et al. | |
| 8,585,572 B2 | 11/2013 | Mehmanesh | |
| 8,747,386 B2 | 6/2014 | Rykhus, Jr. et al. | |
| 8,876,850 B1 * | 11/2014 | Vollmers ............ | A61M 60/869 606/191 |
| 8,882,653 B2 | 11/2014 | Gillespie, Jr. et al. | |
| 8,956,379 B2 | 2/2015 | Luciano et al. | |
| 9,017,359 B2 | 4/2015 | Scandurra et al. | |
| 9,039,725 B1 | 5/2015 | Vollmers et al. | |
| 9,107,992 B2 | 8/2015 | Kushwaha et al. | |
| 9,242,082 B2 | 1/2016 | Vollmers et al. | |
| 9,333,328 B2 | 5/2016 | Scandurra et al. | |
| 9,610,391 B2 | 4/2017 | Vollmers et al. | |
| 9,801,989 B2 | 10/2017 | Vollmers et al. | |
| 9,987,153 B2 | 6/2018 | Scandurra et al. | |
| 10,327,880 B2 | 6/2019 | Connors et al. | |
| 10,350,397 B2 | 7/2019 | Scandurra et al. | |
| 10,376,681 B2 | 8/2019 | Bak-Boychuk et al. | |
| 10,617,538 B2 | 4/2020 | Scandurra et al. | |
| 10,682,448 B2 | 6/2020 | Vollmers et al. | |
| 10,702,682 B2 | 7/2020 | Scandurra et al. | |
| 10,751,519 B2 | 8/2020 | Scandurra et al. | |
| 11,141,581 B2 * | 10/2021 | Vollmers ............ | C01B 17/4515 |
| 11,331,105 B2 | 5/2022 | Gainor et al. | |
| 2001/0023332 A1 | 9/2001 | Hahnen | |
| 2003/0055465 A1 | 3/2003 | Ben-Haim et al. | |
| 2003/0208259 A1 | 11/2003 | Penhasi | |
| 2004/0093007 A1 | 5/2004 | Sussman et al. | |
| 2004/0106971 A1 | 6/2004 | Schwartz et al. | |
| 2004/0111006 A1 | 6/2004 | Alferness et al. | |
| 2004/0143319 A1 | 7/2004 | Schwartz et al. | |
| 2004/0210304 A1 | 10/2004 | Seguin et al. | |
| 2005/0015107 A1 | 1/2005 | O'Brien | |
| 2005/0059965 A1 | 3/2005 | Eberl et al. | |
| 2005/0070938 A1 | 3/2005 | Copa et al. | |
| 2005/0131451 A1 | 6/2005 | Kleshinski et al. | |
| 2005/0251175 A1 | 11/2005 | Weisenburgh et al. | |
| 2005/0267596 A1 | 12/2005 | Chen et al. | |
| 2006/0085028 A1 | 4/2006 | Boock | |
| 2006/0093642 A1 | 5/2006 | Ranade | |
| 2006/0106450 A1 | 5/2006 | Ben Muvhar | |
| 2006/0129083 A1 | 6/2006 | Brenneman et al. | |
| 2006/0135962 A1 | 6/2006 | Kick et al. | |
| 2006/0155310 A1 | 7/2006 | Binmoeller | |
| 2006/0241745 A1 | 10/2006 | Solem | |
| 2006/0253095 A1 | 11/2006 | Stull | |
| 2007/0142819 A1 | 6/2007 | El-Nounou et al. | |
| 2007/0156013 A1 | 7/2007 | Birk | |
| 2007/0156167 A1 | 7/2007 | Connors et al. | |
| 2007/0293848 A1 | 12/2007 | Endo et al. | |
| 2008/0114338 A1 | 5/2008 | Kumar | |
| 2008/0132750 A1 | 6/2008 | Miller | |
| 2008/0147181 A1 | 6/2008 | Ghione et al. | |
| 2008/0194905 A1 | 8/2008 | Walsh | |
| 2008/0195174 A1 | 8/2008 | Walker et al. | |
| 2008/0243093 A1 | 10/2008 | Kalpin et al. | |
| 2008/0312679 A1 | 12/2008 | Hardert et al. | |
| 2009/0143837 A1 | 6/2009 | Rossing et al. | |
| 2009/0222083 A1 | 9/2009 | Nguyen et al. | |
| 2009/0240277 A1 | 9/2009 | Connors et al. | |
| 2009/0294031 A1 | 12/2009 | Pepper et al. | |
| 2010/0042070 A1 | 2/2010 | Gill et al. | |
| 2010/0099945 A1 | 4/2010 | Birk et al. | |
| 2010/0185049 A1 | 7/2010 | Birk et al. | |
| 2010/0197994 A1 | 8/2010 | Mehmanesh | |
| 2010/0204590 A1 | 8/2010 | Hatib et al. | |
| 2010/0274221 A1 | 10/2010 | Sigg et al. | |
| 2010/0324472 A1 | 12/2010 | Wulfman | |

(56) References Cited

U.S. PATENT DOCUMENTS

| | | | |
|---|---|---|---|
| 2010/0331767 A1 | 12/2010 | Frankowski et al. | |
| 2011/0124951 A1 | 5/2011 | Walsh | |
| 2011/0137210 A1 | 6/2011 | Johnson | |
| 2011/0137428 A1 | 6/2011 | Terliuc | |
| 2012/0053514 A1 | 3/2012 | Robinson et al. | |
| 2012/0083646 A1 | 4/2012 | Benson | |
| 2012/0172654 A1 | 7/2012 | Bates | |
| 2013/0079871 A1 | 3/2013 | Scandurra et al. | |
| 2013/0165964 A1 | 6/2013 | Vollmers et al. | |
| 2013/0245665 A1* | 9/2013 | Scandurra | A61M 60/497 606/194 |
| 2014/0214149 A1 | 7/2014 | Kuraguntla et al. | |
| 2014/0228878 A1 | 8/2014 | Scandurra et al. | |
| 2014/0370246 A1 | 12/2014 | Hurt | |
| 2015/0196303 A1 | 7/2015 | Seguin | |
| 2015/0216531 A1 | 8/2015 | Seguin | |
| 2015/0282859 A1 | 10/2015 | Bencini et al. | |
| 2015/0352335 A1 | 12/2015 | Moeller | |
| 2015/0366652 A1 | 12/2015 | Connors | |
| 2016/0082169 A1 | 3/2016 | Scandurra et al. | |
| 2016/0144091 A1 | 5/2016 | Breedon et al. | |
| 2016/0237237 A1 | 8/2016 | Tour et al. | |
| 2016/0310306 A1 | 10/2016 | Brister et al. | |
| 2018/0036464 A1 | 2/2018 | Vollmers et al. | |
| 2019/0192835 A1 | 6/2019 | Scandurra et al. | |
| 2020/0046369 A1 | 2/2020 | Gainor et al. | |
| 2020/0306435 A1 | 10/2020 | Vollmers et al. | |
| 2020/0368507 A1 | 11/2020 | Scandurra et al. | |
| 2021/0069396 A1 | 3/2021 | Vollmers et al. | |

FOREIGN PATENT DOCUMENTS

| | | |
|---|---|---|
| DE | 19508129 A1 | 9/1996 |
| DE | 19508129 C2 | 2/1997 |
| DE | 102005060197 A1 | 6/2007 |
| EP | 0366814 A1 | 5/1990 |
| EP | 0959912 A1 | 12/1999 |
| EP | 0959912 B1 | 9/2004 |
| EP | 2016961 A1 | 1/2009 |
| EP | 2016961 B1 | 2/2010 |
| FR | 3016279 A1 | 7/2015 |
| FR | 3017044 A1 | 8/2015 |
| JP | 2005538807 A | 12/2005 |
| JP | 2007526039 A | 9/2007 |
| JP | 2009502247 A | 1/2009 |
| JP | 2009509650 A | 3/2009 |
| WO | WO-9004430 A1 | 5/1990 |
| WO | WO-9006086 A1 | 6/1990 |
| WO | WO-9317731 A1 | 9/1993 |
| WO | WO-9510317 A1 | 4/1995 |
| WO | WO-9532018 A1 | 11/1995 |
| WO | WO-9600095 A1 | 1/1996 |
| WO | WO-9612518 A1 | 5/1996 |
| WO | WO-9634647 A1 | 11/1996 |
| WO | WO-9850100 A1 | 11/1998 |
| WO | WO-9904833 A1 | 2/1999 |
| WO | WO-0066030 A1 | 11/2000 |
| WO | WO-0236048 A1 | 5/2002 |
| WO | WO-2004026112 A2 | 4/2004 |
| WO | WO-2004080338 A2 | 9/2004 |
| WO | WO-2005084730 A1 | 9/2005 |
| WO | WO-2006020942 A1 | 2/2006 |
| WO | WO-2006067473 A1 | 6/2006 |
| WO | WO-2007014028 A1 | 2/2007 |
| WO | WO-2007038476 A2 | 4/2007 |
| WO | WO-2007059594 A1 | 5/2007 |
| WO | WO-2008154145 A1 | 12/2008 |
| WO | WO-2010022173 A1 | 2/2010 |
| WO | WO-2010129089 A2 | 11/2010 |
| WO | WO-2010129089 A4 | 3/2011 |
| WO | WO-2012071395 A1 | 5/2012 |
| WO | WO-2013109891 A1 | 7/2013 |
| WO | WO-2013148697 A1 | 10/2013 |
| WO | WO-2013185138 A1 | 12/2013 |
| WO | WO-2015102693 A2 | 7/2015 |
| WO | WO-2015107434 A1 | 7/2015 |
| WO | WO-2015114471 A1 | 8/2015 |
| WO | WO-2015133849 A1 | 9/2015 |
| WO | WO-2018075552 A1 | 4/2018 |

OTHER PUBLICATIONS

U.S. Appl. No. 13/884,169, U.S. Pat. No. 9,017,359, filed Nov. 22, 2011 / Apr. 28, 2015.
U.S. Appl. No. 14/253,127, U.S. Pat. No. 9,333,328, filed Apr. 15, 2014 / May 10, 2016.
U.S. Appl. No. 14/309,758, U.S. Pat. No. 8,876,850, filed Jun. 19, 2014 / Nov. 4, 2014.
U.S. Appl. No. 14/531,846, U.S. Pat. No. 9,039,725, filed Nov. 3, 2014 / May 26, 2015.
U.S. Appl. No. 14/710,180, U.S. Pat. No. 9,242,082, filed May 12, 2015 / Jan. 26, 2016.
U.S. Appl. No. 14/955,109, U.S. Pat. No. 10,751,519, filed Dec. 1, 2015 / Aug. 25, 2020.
U.S. Appl. No. 14/956,127, U.S. Pat. No. 10,350,397, filed Dec. 1, 2015 / Jul. 16, 2019.
U.S. Appl. No. 14/990,627, U.S. Pat. No. 9,610,391, filed Jan. 7, 2016 / Apr. 4, 2017.
U.S. Appl. No. 15/474,902, U.S. Pat. No. 9,801,989, filed Mar. 30, 2017 / Oct. 31, 2017.
U.S. Appl. No. 15/785,304, U.S. Pat. No. 10,682,448, filed Oct. 16, 2017 / Jun. 16, 2020.
U.S. Appl. No. 15/993,572, U.S. Pat. No. 10,617,538, filed May 30, 2018 / Apr. 14, 2020.
U.S. Appl. No. 16/288,088, U.S. Pat. No. 10,702,682, filed Feb. 27, 2019 / Jul. 7, 2020.
U.S. Appl. No. 16/342,968, filed Apr. 17, 2019.
U.S. Appl. No. 16/842,612, filed Apr. 7, 2020.
U.S. Appl. No. 16/900,794, filed Jun. 12, 2020.
U.S. Appl. No. 16/989,830, filed Aug. 10, 2020.
U.S. Appl. No. 17/011,870, U.S. Pat. No. 11,141,581, filed Sep. 3, 2020 / Oct. 12, 2021.
U.S. Appl. No. 17/356,410, filed Jun. 23, 2021.
"Aria CV Awarded Top Prize At TCT's 2018 Shark Tank Competition",https://cathlabdigest.com/content/Aria-CV-Awarded-Top-Prize-TCT's-2018-Shark-Tank-Competition,dated Oct. 9, 2018, (accessed Dec. 13, 2019).
"Aria CV Wins Contest for Pulmonary Arterial Hypertension Medical Device," https://pulmonaryhypertensionnews.com/2018/09/27/aria-cv-wins-contest-pulmonary-arterial-hypertension-medical-device/, dated Sep. 27, 2018, (accessed Dec. 13, 2019).
"Aria CV Wins top honors in device organization Shark Tank Competition," http://www.startribune.com/loe-carlson/271816721, dated Apr. 22, 2019, (accessed Dec. 13, 2019).
Borlaug, et al., Ventricular-Vascular Interaction in Heart Failure, Heart Failure Clinics, 4(1):23-36 (2008).
Brian, Jr., M.D., Johnny E., Associate Professor, Department of Anesthesia, University of Iowa College of Medicine, "Gas Exchange, Partial Pressure Gradients, and the Oxygen Window," Oct. 2001.
Elzinga, et al., Left and Right Ventricular Pump Function and Consequences of Having Two Pumps in One Heart, Circ Res, 46:564-574 (1980).
Elzinga, et al., Pressure and Flow Generated by the Left Ventricle Against Different Impedances, Circulation Research, 32(2): 178-186 (1973).
Extended European Search Report dated Mar. 1, 2017 in EP Patent Appl. Serial No. EP11792905.9.
Extended European Search Report dated Feb. 6, 2018 in EP Patent Appl. Serial No. 11843546.0, 7 pages.
Extended European Search Report dated Jun. 19, 2019 in EP Patent Appl. Serial No. EP19165162.9, 5 pages.
Grant, et al., Clinical Significance of Pulmonary Arterial Input Impedance, European Respiratory Journal, 9(11):2196-2199 (1996).
Harnek, et al., Transcatheter Implantation of the MONARC Coronary Sinus Device for Mitral Regurgitation: 1-Year Results from the EVOLUTION Phase I Study (Clinical Evaluation of the Edwards

(56) References Cited

OTHER PUBLICATIONS

Lifesciences Percutaneous Mitral Annuloplasty System for the Treatment of Mitral Regurgitation), JACC: Cardiovascular Interventions 4.1 (2011): 115-122 (2011).

International Search Report & Written Opinion dated Nov. 27, 2020 in Int'l PCT Patent Appl. Serial No. PCT/US2020/049252.

International Search Report & Written Opinion dated Jan. 31, 2018 in Int'l PCT Patent Application Serial No. PCT/US2017/057035.

International Search Report and Written Opinion dated Dec. 22, 2015 in Int'l PCT Patent Application Serial No. PCT/US2015/036201.

International Search Report dated Sep. 8, 2011 in PCT Patent Application No. PCT/US2011/38558.

Lammers, et al., Mechanics and Function of the Pulmonary Vasculature: Implications For Pulmonary Vascular Disease and Right Ventricular Function, Comprehensive Physiology, 2:295-319 (2012).

Lankhaar, et al., Pulmonary Vascular Resistance and Compliance Stay Inversely Related During Treatment of Pulmonary Hypertension, European Heart Journal, 29:1688-1695 (2008).

Lategola, Michael T., Measurement of Total Pressure of Dissolved Gas in Mammalian Tissue In Vivo, J. Appi. Physiol., 19:322-4 (1964).

Loring, Stephen H., et al., Gas Exchange in Body Cavities, Handbook of Physiology—The Respiratory System IV, Chapter 15, pp. 283-295 (1987).

Mahapatra, et al., Relationship of Pulmonary Arterial Capacitance and Mortality in Idiopathic Pulmonary Arterial Hypertension, Journal of the American College of Cardiology, 47(4), 799-803 (2006).

Naeije, et al., Right Ventricular Function in Pulmonary Hypertension: Physiological Concepts, European heart journal supplements, 9.suppl H: H5-H9 (2007).

Partial Search Report dated Oct. 8, 2021 in Int'l PCT Patent Appl. Serial No. PCT/US2021/038771.

PCT International Search Report dated Mar. 8, 2012 in International PCT Patent Application Serial No. PCT/US11/061815.

Pellegrini, et al., Prognostic Relevance of Pulmonary Arterial Compliance in Patients With Chronic Heart Failure, Chest, Original Research, Pulmonary Vascular Disease, 145(5):1064-1070 (2014).

Piiper, Johannes, Physiological Equilibria of Gas Cavities in the Body, Handbook of Physiology. Section 3: Respiration, vol. II, pp. 1205-1218 (1965).

Procyrion., A tool for the Cardiologist, published Jul. 3, 2013. http://web.archive.org/web/20130703020540/http://www.procyrion.com/techno-logy.

Reuben, S. R., Compliance of the Human Pulmonary Arterial System in Disease, Circulation Research, 29(1), 40-50 (1971).

Saouti, et al., The Arterial Load in Pulmonary Hypertension, European Respiratory Review, 19(117):197-203 (2010).

Second Written Opinion dated Jul. 7, 2016 in Int'l PCT Patent Application Serial No. PCT/US2015/036201.

Souza, Rogerio, Assessment of Compliance in Pulmonary Arterial Hypertension, European Heart Journal, 29:1603-1604 (2008).

Sunagawa, et al., Left Ventricular Interaction with Arterial Load Studied in Isolated Canine Ventricle, American Journal of Physiology—Heart and Circulatory Physiology, 245(5), H773-H780 (1983).

Tenney, et al., Gas Transfers in a Sulfur Hexafluoride Pneumoperitoneum, Journal of Applied Physiology, 6(4):201-208 (1953).

Tucker, et al., Inert Gas Exchange in Subcutaneous Gas Pockets of Air-Breathing Animals: Theory and Measurement, Respiration Physiology, 1:151-171 (1966).

Wang, et al., Pulmonary Vascular Wall Stiffness: an Important Contributor to the Increased Right Ventricular Afterload with Pulmonary Hypertension, Pulmonary circulation, 1(2), 212-223 (2011).

Written Opinion dated Mar. 8, 2012 in International PCT Patent Application Serial No. PCT/US11/061815.

Written Opinion dated Sep. 8, 2011 in International PCT Patent Application Serial No. PCT/US11/038558.

International Search Report & Written Opinion dated Nov. 29, 2021 in Int'l PCT Patent Appl. Serial No. PCT/US2021/038771.

\* cited by examiner

DIFFUSION AND INFUSION RESISTANT IMPLANTABLE DEVICES FOR REDUCING PULSATILE PRESSURE

CROSS-REFERENCE TO RELATED APPLICATIONS

This application is a continuation of U.S. patent application Ser. No. 17/011,870, filed Sep. 3, 2020, now U.S. Pat. No. 11,141,581, which claims the benefit of priority of U.S. Provisional Patent Application No. 62/897,166, filed Sep. 6, 2019, the entire contents of each of which are incorporated herein by reference.

FIELD OF THE INVENTION

This application generally relates to diffusion and infusion-resistant implantable devices for, for example, reducing pulsatile load in the pulmonary artery to treat conditions such as pulmonary hypertension.

BACKGROUND OF THE INVENTION

Pulmonary hypertension (PH) is defined as a rise in mean pressure in the main pulmonary artery. PH may arise from many different causes, but, in all patients, has been shown to increase mortality rate. A deadly form of PH arises in the very small branches of the pulmonary arteries and is known as Pulmonary Arterial Hypertension (PAH). In PAH, the cells inside the small arteries multiply due to injury or disease, decreasing the area inside of the artery and thickening the arterial wall. As a result, these small pulmonary arteries narrow and stiffen, causing blood flow to become restricted and upstream pressures to rise. In addition to this increase in resistance to flow, the normally highly elastic pulmonary arteries stiffen. This stiffening, or reduction in compliance, increases the workload on the right ventricle, contributing to right heart failure, the ultimate cause of death in pulmonary hypertension. This increase in stiffness and pressure in the main pulmonary artery is the common connection between all forms of PH regardless of underlying cause.

PH causes the larger pulmonary arteries to dilate and stiffen. As the stiffening progresses, the main pulmonary artery is less able to stretch to accommodate each incoming stroke volume. The lack of expansion causes a much larger rise in pressure with each heartbeat (called systolic or peak pressure) than would occur in a healthy, compliant vessel. In between heartbeats, the arteries in a diseased patient do not recoil as they normally would and diastolic pressure and flow through the lungs drops resulting in a reduction in cardiac output. The heart needs to work harder to push the same stroke volume of blood into the stiff artery at a higher pressure. At the same time, the high pulse pressure travels down the pulmonary arteries to the small vessels and activates molecular signaling pathways causing the cells to multiply more rapidly, accelerating disease progression.

As the pressure within the pulmonary artery increases, the right side of the heart enlarges and thickens to compensate, but eventually reaches the point where it cannot continue to pump enough blood through the lungs to satisfy the body's need for oxygenated blood. This progressive reduction of blood flow is first noticed as shortness of breath when exercising. Over time, the right ventricular remodeling progresses and patients lose the ability to maintain a normal daily level of activity and enter end-stage heart failure where the right ventricle dilates and loses its ability to contract, reducing blood flow even further. At the end-stage, the patient mortality rate is high.

Current treatment protocols for PH and Primary PAH include administration of vasodilating pharmaceuticals. Such pharmaceuticals are extremely expensive and not sufficiently effective. Such pharmaceuticals have been shown to be ineffective of dangerous in PH due to the most common causes of left heart disease and lung disease.

Previously known implantable systems having a balloon, conduit, and reservoir have been described. By implanting a balloon having a fluid therein, e.g., a gas that may be compressible, in the pulmonary artery, compliance is restored, and thus the deleterious effects of vessel stiffening are reduced. U.S. Pat. Nos. 9,017,359 and 9,333,328 to Scandurra and U.S. Pat. Nos. 8,876,850, 9,039,725, and 9,242,082 to Vollmers, assigned to the assignee of the present disclosure, the entire disclosure of each of which are incorporated by reference herein, describe exemplary systems and methods.

During right ventricular systole, the increased blood pressure in the pulmonary artery compresses the fluid in a balloon, and forces the fluid out of the balloon through a conduit and into a reservoir, which may be implanted outside of the vascular system. During right ventricular diastole, the drop in blood pressure within the pulmonary artery results in a pressure gradient between the fluid pressure in the reservoir and the deflated balloon in the pulmonary artery. This gradient causes the fluid to flow back through the conduit into the balloon from the reservoir. The effectiveness of the implantable system is influenced by the amount of fluid transferred between the balloon and the reservoir during the cardiac cycle.

As such, it is important that the volume of fluid in the closed system be maintained substantially constant for as long as possible, especially for long-term implantable systems. It is also important to minimize diffusion and infusion of other non-desirable gasses, liquids and vapors through the system surfaces. For example, diffusion of water molecules into the system from the blood may result in the formation of water drops or pools which may impede or restrict the beneficial flow within the system. In addition, gases in the venous blood will attempt to equalize their partial pressure across the balloon of the system independently of other gases in the surrounding mixture of gases, resulting in diffusion of the gas within the balloon into the patient's vasculature.

As described in the incorporated Scandurra and Vollmers patents, it is beneficial to use a flexible polymeric balloon to reduce energy loss during cyclic function, allow for high cycle count with low risk of fatigue driven failure, maintain biocompatibility, and allow for tight wrapping and small insertion size required for interventional procedures. Accordingly, selection of a fluid, e.g., a liquid or a gas, that does not readily diffuse through a polymeric balloon membrane may assist in reducing diffusion through the membrane of the balloon. Nonetheless, most fluids commonly used and readily available for medical purposes including NO, He, $H_2O$, $CO_2$, $O_2$, $N_2$, Ar, and $CH_4$ will naturally diffuse through the wall of the balloon to equalize its partial pressure inside the balloon with the partial pressure in the venous blood.

There are additional requirements that must be balanced with the reduction in permeability. First, a functional gas preferably diffuses easily into blood so that a failure of the balloon or a system component does not cause a non-soluble gas embolus to occlude blood flow in the vasculature.

Additionally, the preferred gas for a system of the type described in the aforementioned patents should have very low molecular weight in order to optimize gas flow and minimize turbulence and energy loss. For example, $N_2$ tends to diffuse relatively slowly through most polymer membranes, but $N_2$ does not dissolve into blood as well as $CO_2$, and may be considered a risk for embolism. $CO_2$ is a candidate gas due to the very high solubility of the $CO_2$ in blood, but $CO_2$ is a relatively heavy gas molecule, which may cause turbulent flow that could hinder device performance. Additionally, preliminary tests on the compatibility of $CO_2$ with many of the commercially available polymer membranes shows high permeability through such membranes. Although $CO_2$ diffuses through polymers fairly readily, it does so at a rate slower than that of helium. Helium is a candidate gas due to a relatively high solubility in blood and a very low molecular size, which helps to optimize gas flow through the implantable system.

Another approach to reducing diffusion of a gas through the implantable system involves selecting a material that minimizes gas diffusion. However, a balance must be achieved between the reduction of permeability and the functionality of the device. A preferred balloon would be easily deformable when exposed to the pressures encountered in the pulmonary artery. Because the balloon should survive long-term, e.g., for millions of cycles, trade-offs must be made between rigidity and durability. In particular, energy expended in deforming the polymer of the balloon rather than moving gas through the system is lost as noise, friction, or heat, and cannot be recovered during right ventricular diastole, reducing the energetic efficiency of the device. Additionally, there is a general relation between rigidity and durability according to which a more rigid polymeric balloon is more likely to crease and buckle, ultimately resulting in polymer fatigue and loss of balloon integrity.

Relative permeability rates of balloon materials and common gases are known, for example, for polyethylene, polyurethane, polyurethane/polycarbonate blends, polyvinylidine fluoride, polyvinylidine chloride, polydimethylsiloxane, butyl, neoprene, nitrile, nylon, silicone, PEEK, polytetrafluoroethene, and composite blends of many of these materials. In addition, the concept of adding additional materials and layers to existing materials to form composites or multilayer materials is also possible. In some situations, adding a particulate to the polymer to improve the vapor barrier properties of a material has been demonstrated to reduce diffusion of a gas through the material. For example, nanoclay platelets, a material with a large aspect ratio of diameter to thickness, may be compounded into a polymer with these platelets lying flat along the plane of the film. The clay nanoparticle itself is impermeable to gas, so the gas must pass around these platelets to migrate through the film. The passage of gas through a vapor barrier containing layers of these nanoclay platelets is greatly impeded due to the tortuous path that the gas must follow to navigate, resulting in a much slower gas transfer rate than that of the base polymer. While some reduction in gas diffusion has been observed through material selection, it would be desirable to have materials with reduced diffusion to a level suitable for use in a clinical device intended for long-term implantation, e.g., a period of several weeks to years. Such materials would reduce the frequency of periodic fluid refills in the implantable long-term system which may be inconvenient for the patient.

Example publications include: R. W. Tucker, et al., "Inert Gas Exchange in Subcutaneous Gas Pockets of Air-Breathing Animals: Theory and Measurement," Respiration Physiology, 1, 151-171 (1966); Loring, Stephen H., et al., "Gas Exchange in Body Cavities," Handbook of Physiology—The Respiratory System IV, 283-295; Brian, Jr., Johnny E., "Gas Exchange, Partial Pressure Gradients, and the Oxygen Window," available at: http://www.tek-dive.com/uploads/brian_oxygen_window.pdf; S. M. Tenney, et al., "Gas Transfers in a Sulfur Hexafluoride Pneumoperitoneum," Journal of Applied Physiology, Vol. 6, Number 4, 201-208, October 1953; Lategola, Michael T., "Measurement of Total Pressure of Dissolved Gas in Mammalian Tissue In Vivo," available at: https://www.physiology.org/doi/abs/10.1152/jappl.1964.19.2.322; Piiper, Johannes, "Physiological Equilibria of Gas Cavities in the Body," Handbook of Physiology—Respiration II, 1205-1218.

It would be desirable to provide systems and methods for treating heart disease, such as pulmonary hypertension and right heart failure, where the period between refilling the fluid may be extended as long as possible to provide patient convenience and safety, as well as device efficacy.

It further would be desirable to provide systems and methods for treating heart disease having a fluid mixture selected to effectively reduce or eliminate diffusion of the internal fluid out of, and infusion of external fluid into, the implantable system, in addition to selecting a fluid that does not readily diffuse through the material.

SUMMARY OF THE INVENTION

The present invention provides fluid mixtures, e.g., gas mixtures, that reduce in vivo infusion and diffusion. The gas mixtures may be used in systems and methods for reducing pulsatile pressure. For example, the system may include a balloon sized and shaped to be implanted in a blood vessel, e.g., the pulmonary artery, and to hold a gas mixture pressurized such that the balloon transitions between an expanded state and a collapsed state responsive to pressure fluctuations in the blood vessel. The balloon may be structured for long term implantation in the blood vessel.

The gas mixture preferably includes one or more constituent gases and a diffusion-resistant gas selected to maintain a desired volume and pressure within the balloon throughout multiple cardiac cycles. For example, the gas mixture may be pressurized within the balloon to match blood pressure surrounding the balloon within the blood vessel to reduce permeation of gases across the balloon throughout multiple cardiac cycles. The one or more constituent gases may include, e.g., at least one of NO, He, $H_2O$, $CO_2$, $O_2$, $N_2$, Ar, or $CH_4$. For example, the one or more constituent gases may include $O_2$, $CO_2$, and $N_2$, e.g., 7%±1% $O_2$, 12%±1% $CO_2$ and balance $N_2$. In one embodiment, the one or more constituent fluids consist of 02, $CO_2$, and $N_2$, and the diffusion-resistant fluid consists of sulfur hexafluoride.

The diffusion-resistant gas preferably has a partial pressure equal to a difference between partial pressures of the one or more constituent gases and a predetermined desired balloon pressure. Thus, the diffusion-resistant gas is selected to resist diffusion through the balloon throughout multiple cardiac cycles. For example, the diffusion-resistant gas may be, sulfur hexafluoride or a perfluorinated compound. In addition, the diffusion-resistant gas may make up between 8-25% of the gas mixture within the balloon. The amount of diffusion-resistant fluid may be selected based on the patient's mean pulmonary arterial pressure (mPAP) and/or the patient's altitude of residence. During an initial fill, the fluid mixture may include 15-50 ml of the diffusion-resistant fluid, and an amount of the one or more constituent fluids such that the volume and pressure within the balloon is at a known state. In addition, during the initial fill, the fluid mixture may include an additional 10-40 ml of the one or more constituent fluids. During a fluid check and/or refill procedure, the fluid mixture may include an additional volume of diffusion-resistant fluid that is 8-25% of a desired additional volume of fluid mixture within the balloon, such that the additional volume of diffusion-resistant fluid causes an influx of the one or more constituent fluids into the balloon. Moreover, the diffusion-resistant gas preferably remains in its gaseous phase at body temperature of a patient. The amount of the fluid mixture within the balloon may be repeatedly adjusted to maintain the desired volume or pressure within the balloon.

In addition, the system may include a reservoir sized and shaped to hold the gas mixture, and a conduit having a proximal end coupled to the reservoir and a distal end coupled to the balloon to provide fluidic communication between the reservoir and the balloon. The reservoir may include a septum for allowing the addition of fluid to or the removal of fluid from the reservoir and to permit repeated needle penetrations while maintaining a fluid-tight seal. Moreover, the system may include an anchor for securing the balloon within the vessel. The anchor may be structured to remain within the vessel as the balloon is removed and replaced periodically.

In accordance with another aspect of the present invention, a fluid mixture for use within an implantable system including a balloon implantable within a blood vessel is described. The fluid mixture may include one or more constituent fluids mixed with sulfur hexafluoride. The one or more constituent fluids may include $O_2$, $CO_2$, and $N_2$. For example, a mixture of the one or more constituent fluids, prior to mixing with sulfur hexafluoride, may consist of 7%±1% $O_2$, 12%±1% $CO_2$ and balance $N_2$.

In accordance with yet another aspect of the present invention, a method for introducing fluids into an implantable system is described. The method may include implanting the balloon within a blood vessel of the patient, e.g., the pulmonary artery; introducing a diffusion-resistant fluid, e.g., sulfur hexafluoride, into the balloon; introducing one or more constituent fluids into the balloon in an amount to reach a known state; and introducing an additional amount of the one or more constituent fluids into the balloon. The diffusion-resistant fluid and the one or more constituent fluids within the balloon may be pressurized such that the balloon is transitionable between an expanded state and a collapsed state responsive to pressure fluctuations in the blood vessel.

The method further may include permitting the one or more constituent gases to equilibrate across the balloon according to their respective partial pressure gradient across the balloon for a time period. The balloon may transition between the expanded state and the collapsed state responsive to pressure fluctuations in the blood vessel while reducing permeation of fluids across the balloon throughout multiple cardiac cycles. In addition, prior to introducing the diffusion-resistant fluid, the method may include flushing the balloon with one or more constituent fluids. The balloon may be injected with a volume of the diffusion-resistant gas such that the diffusion-resistant gas makes up between 8-25% of a total volume of the diffusion-resistant gas and the one or more fluids within the balloon. The balloon may be injected with gas via a conduit coupled to the balloon. In addition, the balloon may be injected with gas via a reservoir coupled to the conduit coupled to the balloon. For example, the reservoir may be pierced at a septum to inject gas into the reservoir. Such gas is permitted to travel between the reservoir and the balloon via the conduit.

The method may include adjusting an amount of the diffusion-resistant gas within the balloon based on an amount of the one or more constituent fluids equalized within the balloon after a time period. For example, an additional amount of diffusion-resistant gas may be introduced to the balloon if a total amount of gas within the balloon after the time period is below a predetermined threshold and gas may be extracted from the balloon if the total amount of gas within the balloon after the time period is above the predetermined threshold.

The method further may include checking one or more parameters of the balloon; determining a volume of the diffusion-resistant fluid and the one or more constituent fluids within the balloon; determining an amount of diffusion-resistant fluid to be added to the balloon; and introducing the determined amount of diffusion-resistant fluid into the balloon. Moreover, the method may include comparing the determined volume of the diffusion-resistant fluid and the one or more constituent fluids within the balloon to a desired volume of the balloon to calculate a volume difference, and determining an amount of diffusion-resistant fluid to be added to the balloon based on the calculated volume difference. Accordingly, the determined amount of diffusion-resistant fluid introduced into the balloon may be based on the calculated volume difference and at least one of the patient's mean pulmonary arterial pressure (mPAP) or altitude of residence. In some embodiments, the method may include forming a fluid mixture having the determined amount of diffusion-resistant fluid and one or more constituent fluids. The fluid mixture may be introduced into the balloon until one or more parameters reach a predetermined state, e.g., when reservoir pulse pressure has peaked and/or begins to decline, and/or the diastolic pressure increases at a predetermined rate.

The determined amount of diffusion-resistant fluid may be 8-25% of the calculated volume difference, such that the determined amount of diffusion-resistant fluid causes an influx of the one or more constituent fluids into the balloon over multiple cardiac cycles. In addition, the determined amount of diffusion-resistant fluid may be less than the calculated volume difference. The method further may include implanting a conduit and a reservoir such that the balloon, the conduit, and the reservoir are fluidicly coupled in an implanted system. Accordingly, introducing the diffusion-resistant fluid into the balloon, introducing the one or more constituent fluids into the balloon, and introducing the additional amount of the one or more constituent fluids may include introducing via injection into the reservoir.

In accordance with another aspect of the present invention, a method of adjusting an amount of the diffusion-resistant fluid within a balloon implanted in a blood vessel is provided. The method may include checking one or more parameters of the balloon; determining a volume of the diffusion-resistant fluid and one or more constituent fluids within the balloon; determining an amount of diffusion-resistant fluid to be added to the balloon; and introducing the determined amount of diffusion-resistant fluid into the balloon. The method further may include comparing the determined volume of the diffusion-resistant fluid and the one or more constituent fluids within the balloon to a desired volume of the balloon to calculate a volume difference, such that the determined amount of diffusion-resistant fluid is based on the calculated volume difference. Moreover, the method may include stopping introduction of the determined amount of diffusion-resistant fluid when a predetermined state is reached.

In accordance with yet another aspect of the present invention, the method for introducing fluids into an implantable system may include implanting the balloon within the blood vessel of the patient; injecting the balloon with the one or more fluids; permitting the one or more constituent gases to equilibrate across the balloon according to their respective partial pressure gradient; injecting the balloon with a diffusion-resistant gas, the diffusion-resistant gas and the equalized one or more constituent gases pressurized such that the balloon is transitionable between an expanded state and a collapsed state responsive to pressure fluctuations in the blood vessel; and/or transitioning the balloon between the expanded state and the collapsed state responsive to pressure fluctuations in the blood vessel while reducing permeation of gases across the balloon throughout multiple cardiac cycles. For example, injecting the balloon with the diffusion-resistant gas may include injecting the balloon with the diffusion-resistant gas within a week of injecting the balloon with the one or more constituent gases.

DETAILED DESCRIPTION OF THE INVENTION

Systems and methods of the present disclosure include diffusion and infusion-resistant fluid mixtures for implantable devices. The implantable devices may be used for restoring compliance to a portion of a patient's vasculature, such as the pulmonary system. In accordance with the principles of the present disclosure, the systems may be optimized for use in treating all forms of pulmonary hypertension (PH) as described in the World Health Organization Clinical Classification, including Pulmonary Arterial Hypertension (PAH), and right heart failure (RHF).

Figure 1A:
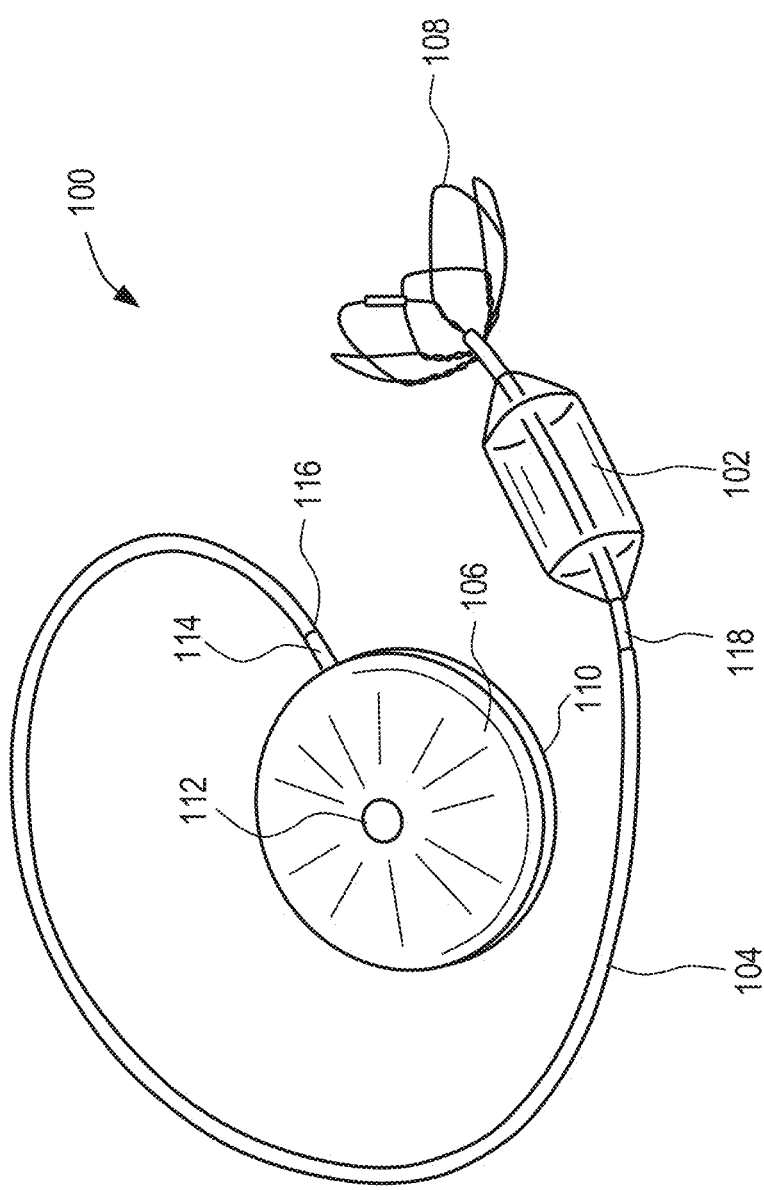
FIG. 1A-1C schematically illustrate components of exemplary configurations of an implantable device that may be filled with a fluid mixture, in accordance with some aspects of the present disclosure.

Referring to FIG. 1A, an overview of an exemplary system constructed in accordance with the principles of the present disclosure is provided. System 100 may include compliant body 102, conduit 104, and reservoir 106 as described in U.S. Pat. No. 8,876,850 to Vollmers and U.S. Pat. No. 9,017,359 to Scandurra, and U.S. Provisional Patent Application No. 63/044,337 to Harder, the entire contents of each of which are incorporated by reference herein. For example, compliant body 102 may be secured within the body lumen via anchor 108. Anchor 108 may be coupled to compliant body 102, to conduit 104 proximal to compliant body 102, and/or to conduit 104 distal to compliant body 102 as illustrated. Preferably, anchor 108 is configured to expand from a contracted state, e.g., when compressed in a sheath, to an expanded state responsive to an event, e.g., exposure from the sheath or expansion of compliant body 102. In the expanded state, anchor 108 is sized to contact the inner wall of the body lumen or another anchor deployed within the body lumen.

Conduit 104 is configured to couple compliant body 102 to reservoir 106. Conduit 104 includes proximal region 116 and distal region 118. In the illustrated embodiment, conduit 104 is coupled to port 114 of reservoir 106 at proximal region 116 and coupled to compliant body 102 at distal region 118. Preferably, conduit 104 has a length suitable to extend from reservoir 106 in the subcutaneous space, through the subclavian vein, and past the pulmonary valve to compliant body 102 implanted within the pulmonary artery. Preferably, conduit 104 extends through and past compliant body 102 a predetermined distance and includes one or more ports in the portion of conduit 104 within compliant body 102 to permit fluid, e.g., a compressible gas mixture, to be introduced from conduit 104 into the interior space of compliant body 102. In one embodiment, conduit 104 has a length between about 20-150 cm, and more preferably about 100 cm. The diameter of conduit 104 is preferably about 3-5 mm or about 4 mm at distal region and may be variable along the length of conduit 104 up to a predetermined maximum diameter, e.g., about 15 mm. Preferably, conduit 104 has a wall/membrane thickness between about 0.005 to 0.050 inches.

As described above, at least a portion of conduit 104 may extend through and past compliant body 102. As such, the surface of the conduit 104 within compliant body 102 may be coated with compliant material or porous compliant material which acts to cushion the surface of the conduit. Suitable materials may include polymers, open cell foamed rubber, foamed rubber, silicones, woven or knitted fibers, dense brush-type materials such as Velcro, and the like. Such coatings will prevent acoustic pressure spikes in the surrounding blood when the compliant body collapses completely.

Compliant body 102, e.g., a balloon, is adapted to be implanted in a body lumen, e.g., the pulmonary artery which includes the main pulmonary artery and the pulmonary artery branches. Preferably, compliant body 102 is configured for long-term implantation within the body lumen, e.g., from a period of several weeks, months or years. With each heartbeat, fluid within system 100 moves towards or away from compliant body 102. By collapsing and getting smaller in volume, compliant body 102 mimics the expansion of the vessel (increasing intravascular volume) that naturally occurs in a healthy person, making room for incoming blood. This collapsing action has the effect of absorbing or reducing the peak systolic pressure and also reducing the rate of change (e.g., acceleration) of blood flow.

When the heart begins to relax, the pulmonary valve closes and the pressure in the main pulmonary artery begins to drop. As the pressure drops below the pressure level in reservoir 106, fluid flows from reservoir 106 to compliant body 102 such that the potential energy within compliant body 102 increases. During diastole, compliant body 102 preferably expands to about the full volume of compliant body 102 to increase pressure in the pulmonary artery to push additional blood through the artery towards the lungs, thereby increasing cardiac output. Continuous expansion and collapse of compliant body 102 is expected to reduce peak systolic pressure and increase diastolic pressure, thus reducing the load on the right ventricle and increasing heart efficiency. Preferably compliant body 102 is designed to handle multiple expansion and collapse cycles continuously over the course of long-term implantation, e.g., over a period of weeks, months or years.

Compliant body 102 has a maximum diameter, a length, and a wall/membrane thickness. Preferably, compliant body 102 has a maximum diameter between about 1.5-3.5 cm, and preferably about 2.5 cm; a length between about 3-8 cm, and preferably about 5-6 cm; and a wall/membrane thickness between about 0.001-0.020 inches. Compliant body 102 preferably has a diameter in the fully expanded state that is less than the diameter of the pulmonary artery. For example, the diameter of compliant body 102 in the fully expanded state may be between about 20-90%, and more preferably about 50-70%, of the diameter of the pulmonary artery in the area at which compliant body 102 is implanted. Applicant has discovered that utilizing a compliant body sized such that the ratio of the inner diameter of the body lumen to the maximum balloon diameter is below a predetermined threshold, e.g., from about 0.9 to about 0.6, maintains pressure upstream from the compliant body at a level substantially similar to pressure downstream from the compliant body, thereby regulating pressure drop across the compliant body during the cardiac cycle. Compliant body 102 is preferably sized with a maximum diameter that will not obstruct blood flow or increase resistance to flow in the pulmonary artery.

The surface of compliant body 102 may be biomimetic, have antithrombotic properties, and/or the external surface compliant body 102 may be coated with a material to prevent thrombus formation, such as heparin or the like. Additionally or alternatively, the surface of compliant body 102 may be lubricious, such that it impedes adhesion of body components such as platelets, proteins, endothelium, endocardium, or heart valves. Additionally or alternatively, the compliant body material or the surface of compliant body 102 may be composed of a material that minimizes chemical or oxidative degradation. Any suitable biocompatible lubricant may be used including, but not limited to, silicone or hyaluronan based materials. The shape of compliant body 102 may also be carefully defined to eliminate dead space in the surrounding blood flow to minimize thrombus formation.

Compliant body 102 is preferably a compliant or semi-compliant balloon and may be formed from one or more materials that resist diffusion of internal fluid out of the system and of external fluid into the system. For example, compliant body 102 may be formed of a carbon-polymer composite such as a graphene-polymer matrix having graphene compounded into a polymer, dispersed in a polymer solution, or a graphene sandwiched between two layers of polymer, as described in U.S. Patent Pub. No. 2020/0046369 to Gainor, the entire contents of which are incorporated herein by reference. Alternatively, compliant body 102 may be formed of polyvynalidine.

Figure 1B:
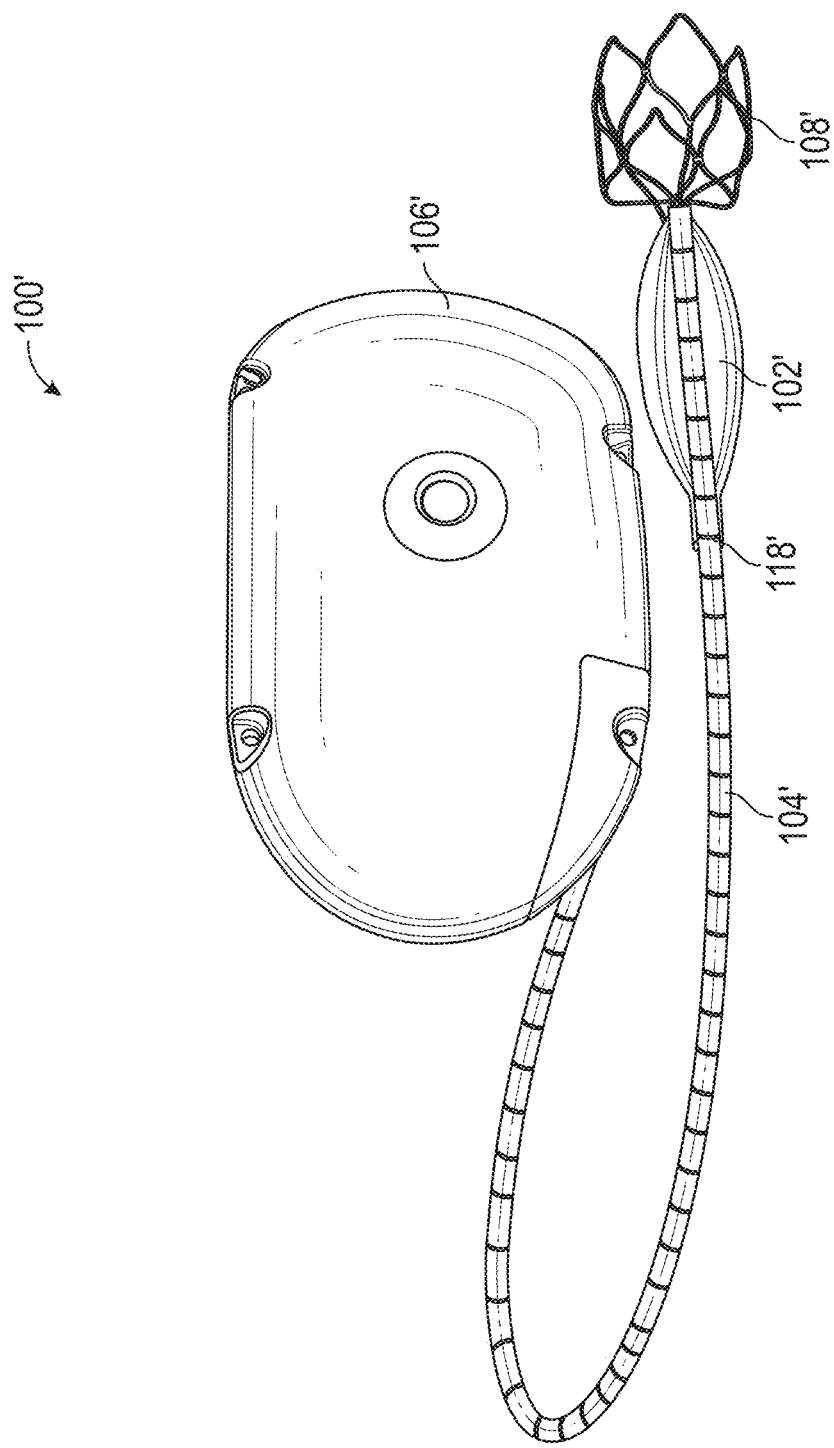

System 100' illustrated in FIG. 1B may be configured similarly as system 100 described with reference to FIG. 1A. For example, system 100' may include detachable compliant body 102' which may be configured similarly as detachable compliant body 102, conduit 104' which may be configured similarly as conduit 104, reservoir 106' which may be configured similarly as reservoir 106, and anchor 108' which may be configured similarly as anchor 108. Reservoir 106' is shaped for subcutaneous implantation. In a preferred embodiment, reservoir 106' is designed to be implanted subcutaneously in the axilla. Conduit 104' is coupled to reservoir 106' and compliant body 102' and includes a distal region 118'. Anchor 108' is configured to detachably secure compliant body 102' at any suitable portion of any suitable blood vessel, such as the pulmonary artery, for example any suitable portion of the main pulmonary artery and/or one or more of the pulmonary artery branches, in a manner such as described with reference to FIG. 1A. For example, anchor 108' may be implanted within a pulmonary artery branch to anchor compliant body 102' in the main pulmonary artery. As used herein, pulmonary artery includes the main pulmonary artery and the pulmonary artery branches. Compliant body 102' may be configured for long-term implantation within the body lumen, e.g., from a period of several weeks, months or years. Compliant body 102' is configured so as to be attachable to and detachable from anchor 108', for example, so as to be movable or removable relative to anchor 108' while anchor 108' is engaged with a blood vessel in a deployed state. Optionally, compliant body 102' may be replaced with another such compliant body 102' as appropriate, as described in greater detail below. In configurations in which compliant body 102' is implanted within a pulmonary artery, with each heartbeat, fluid within system 100' moves away from compliant body 102' to reservoir 106' via conduit 104' and then towards compliant body 102' from reservoir 106' via conduit 104' so as to reduce pulsatile pressure in a manner such as described with reference to FIG. 1A.

Figure 1C:
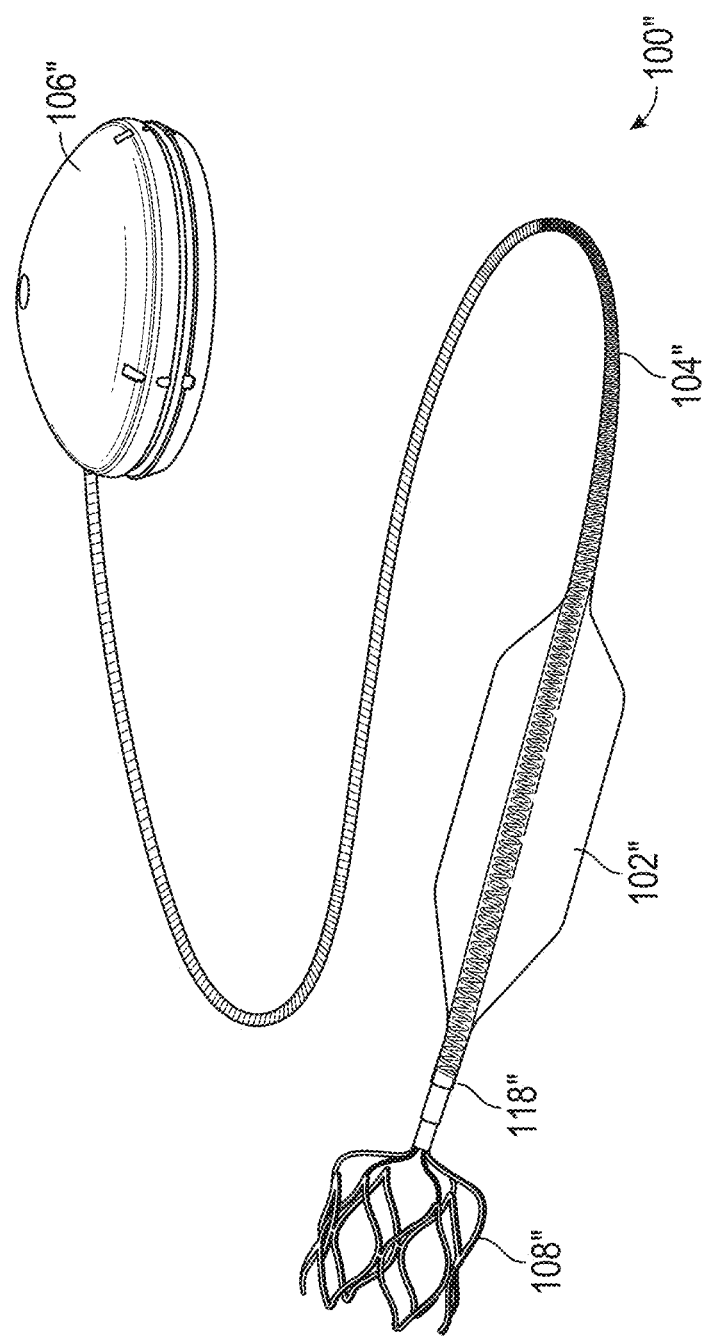
Figure 1D:
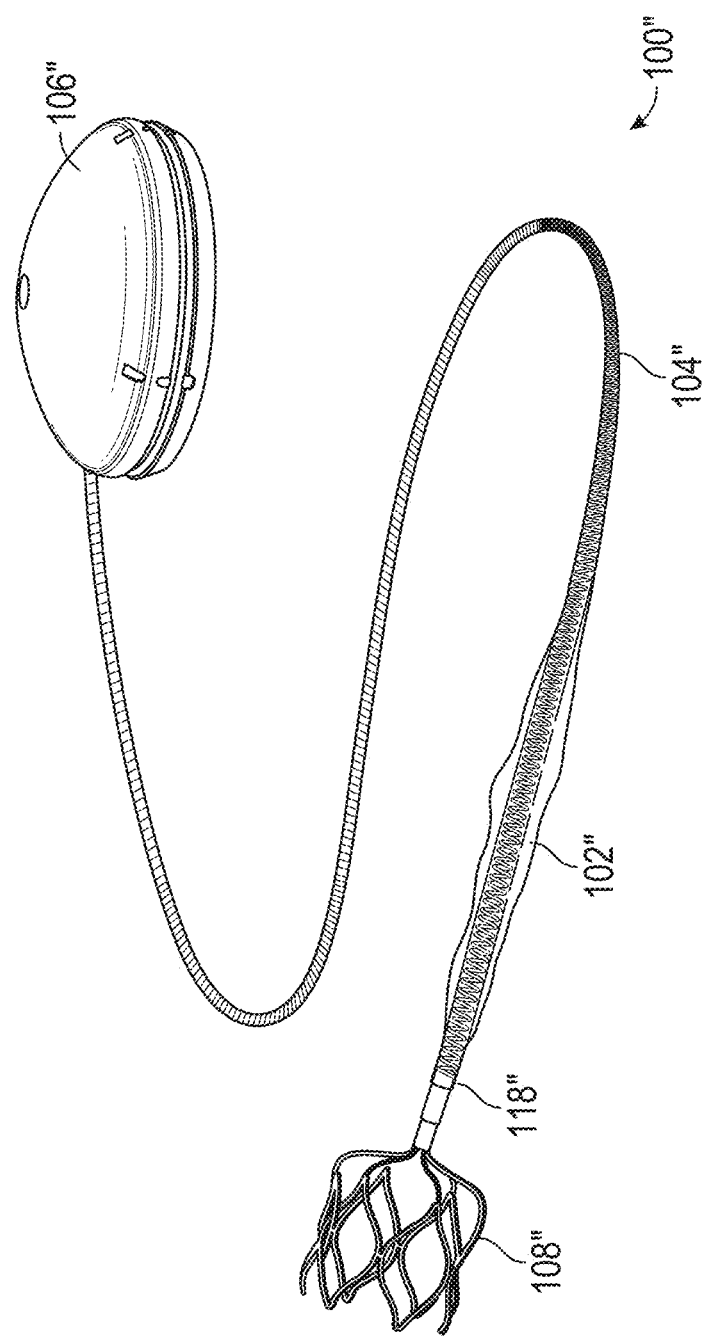
FIG. 1D illustrates the configuration of FIG. 1C with a balloon of the implantable device in a collapsed configuration.

System 100" illustrated in FIG. 1C may be configured similarly as system 100 described with reference to FIG. 1A. For example, system 100" may include detachable compliant body 102" which may be configured similarly as detachable compliant body 102, conduit 104" which may be configured similarly as conduit 104, reservoir 106" which may be configured similarly as reservoir 106, and anchor 108" which may be configured similarly as anchor 108. Reservoir 106" is shaped for subcutaneous implantation. In a preferred embodiment, reservoir 106" is designed to be implanted subcutaneously over the abdomen. Conduit 104" is coupled to reservoir 106" and compliant body 102" and includes a distal region 118". Anchor 108" is configured to detachably secure compliant body 102" at any suitable portion of any suitable blood vessel, such as the pulmonary artery, for example any suitable portion of the main pulmonary artery and/or one or more of the pulmonary artery branches, in a manner such as described with reference to FIG. 1A. FIG. 1D illustrates the configuration of FIG. 1C with the compliant body 102 in a collapsed configuration.

As will be appreciated by those of ordinary skill in the art, a biocompatible fluid, e.g., liquid and/or gas, may be used in systems 100, 100', 100". The fluid may be a compressible gas such that the volume of the gas changes in response to a change in pressure in the artery (or other implantation location of the compliant body) consistent with the gas bulk modulus of the gas. Furthermore, the gas is preferably nontoxic, easily absorbed by the body, and has physical properties that resist diffusion through the wall of the compliant body. Suitable gases may include, but are not limited to, nitrogen, carbon dioxide, argon, neon, and helium. Optionally, the gas may have therapeutic properties, such as nitric oxide which causes vasodilation.

However, keeping the compliant body, e.g., compliant body 102, inflated with common components of atmospheric gas when it is surrounded by e.g., venous blood, is difficult due to the differences in gas partial pressures across the membrane of compliant body 102, in particular, due to the low partial pressures of gas(es) in the venous circulation. For example, the partial pressure of a gas in a mixture is proportional to the absolute pressure of the mixture and the fraction of the mixture the gas represents. Gases always attempt to equalize their partial pressure across a semipermeable membrane, independently of other gases in the surrounding mixture.

Moreover, the physiological condition referred to as the "oxygen window" describes how the partial pressure of gases in the arterial, and venous blood are significantly lower and different than that found in the surrounding atmosphere. See, e.g., Brian, Jr., Johnny E., "Gas Exchange, Partial Pressure Gradients, and the Oxygen Window," available at: http://www.tek-dive.com/uploads/brian_oxygen_window.pdf. Specifically, on inspiration, the air becomes saturated with water vapor. This reduces the concentration of all other gases in the mixture. When inspired air arrives at the alveoli, $O_2$ is transmitted to the blood stream while $CO_2$ is transmitted to the gas in the alveoli, reducing $O_2$ levels and increasing $CO_2$ levels in the alveoli and the exhaled breath. The $O_2$ saturation is slightly lower in arterial blood leaving the lungs than that found in the lungs due to the consumption of oxygen by lung tissue. When the blood passes through capillary beds in the body, the oxygen level drops even more as $O_2$ moves into body tissues.

As $CO_2$ diffuses from tissues into blood, the partial pressure of $CO_2$ in the blood increases by approximately 5 mmHg, with much of it being buffered through chemical conversions or attachment to hemoglobin. When $O_2$ and $CO_2$ are buffered or attached to hemoglobin, they do not contribute to the partial pressure of the gases in the blood. When the blood returns to the alveoli, it gains more $O_2$ and discharges $CO_2$. The levels of non-metabolic gases such as $N_2$ and Argon remain constant throughout the circulation. Table 1 below shows the expected partial pressure values and % concentrations for humans at sea level, and Table 2 shows the expected partial pressure values and % concentrations for sheep at Minneapolis/St. Paul altitude. Moreover, changing body temperature changes the water vapor partial pressure.

TABLE 1

Blood partial pressures based on human body temperature at sea level ($P_{atm}$ = 760 mmHg)

| | Inspired air (mmHg) | Inspired Air (%) | Alveolar | Arterial | Venous | Venous % | Venous % excluding $H_2O$ |
|---|---|---|---|---|---|---|---|
| $O_2$ | 159 | 21 | 103 | 95 | 45 | 6 | 6.8 |
| $N_2$ | 601 | 79 | 570 | 570 | 570 | 80.6 | 86.4 |
| $H_2O$ | | | 47 | 47 | 47 | 7 | |
| $CO_2$ | | | 40 | 40 | 45 | 6 | 6.8 |
| Total | 760 | 100 | 760 | 752 | 707 | 100 | 660 |

TABLE 2

Blood partial pressures based on sheep at Minneapolis/St. Paul altitude ($P_{atm}$ = 735 mmHg)

| | Inspired air (mmHg) | Inspired Air (%) | Alveolar | Arterial | Venous | Venous % | Venous % excluding $H_2O$ |
|---|---|---|---|---|---|---|---|
| $O_2$ | 154 | 21 | 99 | 93 | 45 | 6 | 6.8 |
| $N_2$ | 581 | 79 | 543 | 543 | 543 | 78.4 | 82.3 |
| $H_2O$ | | | 53 | 53 | 53 | 8 | |
| $CO_2$ | | | 40 | 40 | 45 | 6 | 6.8 |
| Methane | | | | | 6.8 | 1 | |
| Total | 735 | 100 | 735 | 729 | 693 | 100 | 633 |

Figure 2:
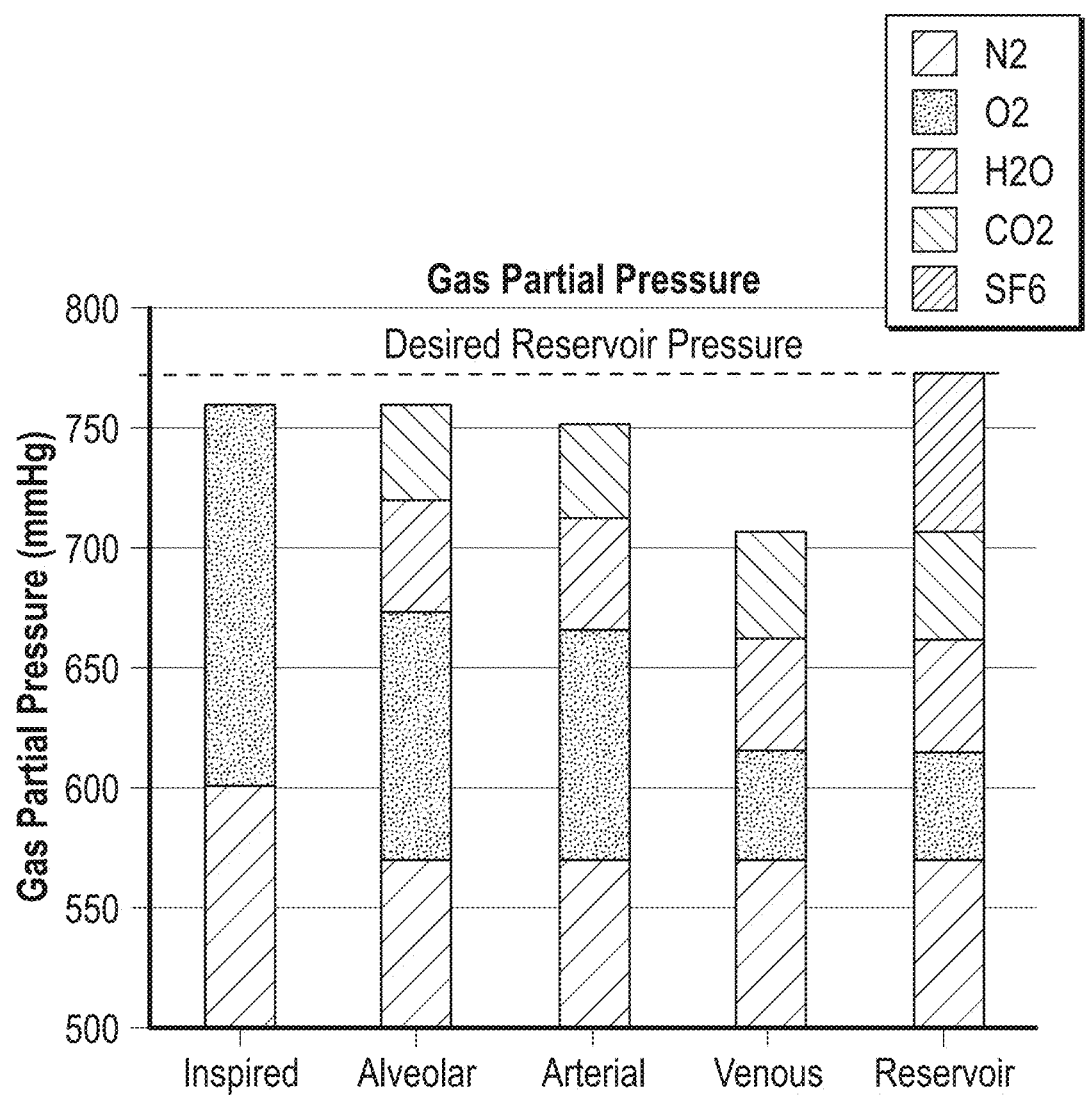
FIG. 2 is a graph illustrating gas partial pressures for various gas mixtures in in vivo and in an exemplary reservoir of the implantable device.

Referring now to FIG. 2, a graphical representation of the partial pressures of gases in humans at sea level is provided. In this representation, the desired pressure of gases in the reservoir, is 775 mmHg or torr. The desired reservoir pressure may be set by pulmonary artery pressure of the patient and the atmospheric pressure at the time. The total of the constituent partial pressures of venous gases is approximately 707 mmHg, and thus, the pressure of gas in the balloon wants to equalize at 707 mmHg, which is below atmospheric pressure and below the desired reservoir pressure. Thus, if the balloon is inflated with a mixture of one or more of the gases present in venous blood, the total pressure will be above that of the total of the partial pressures in venous blood in the pulmonary artery, and there will be a net loss of gas to the venous blood as the partial pressures attempt to equilibrate. To account for the loss of volume of gas within the balloon, the system may repeatedly be topped off, e.g., refilled, but the gases will continue to diffuse out over multiple cardia cycles. $H_2O$ is likely the fastest diffuser through the polymer balloon followed by $CO_2$, then $O_2$ and then $N_2$.

Thus, in accordance with the principles of the present invention, the composition of the fluid(s) injected in system 100 (which includes system 100' or 100") may be selected to match partial pressures of gases in the blood vessel to minimize the infusion or diffusion of gases during operation of system 100, and compliant body 102 may further be topped off with a diffusion-resistant gas having a large molecular weight and a very slow diffusion rate to minimize diffusion of fluid out of and infusion of fluid into system 100. As it may be difficult to fill system 100 with a gas mixture that is saturated with $H_2O$ vapor, an additional amount of $CO_2$, i.e., the sum of the expected amount of $CO_2$ and the expected amount of $H_2O$ that would infuse into balloon 102, may be added to balloon 102 with the expectation that $CO_2$ would diffuse out of balloon 102 at a rate similar to $H_2O$ infusing into balloon 102 to avoid overfilling balloon 102. Thus, the system volume would remain relatively constant. Accordingly, system 100 may be designed such that these diffusion rates are nearly equivalent and the inventive method could utilize the practice described above.

Figure 3A:
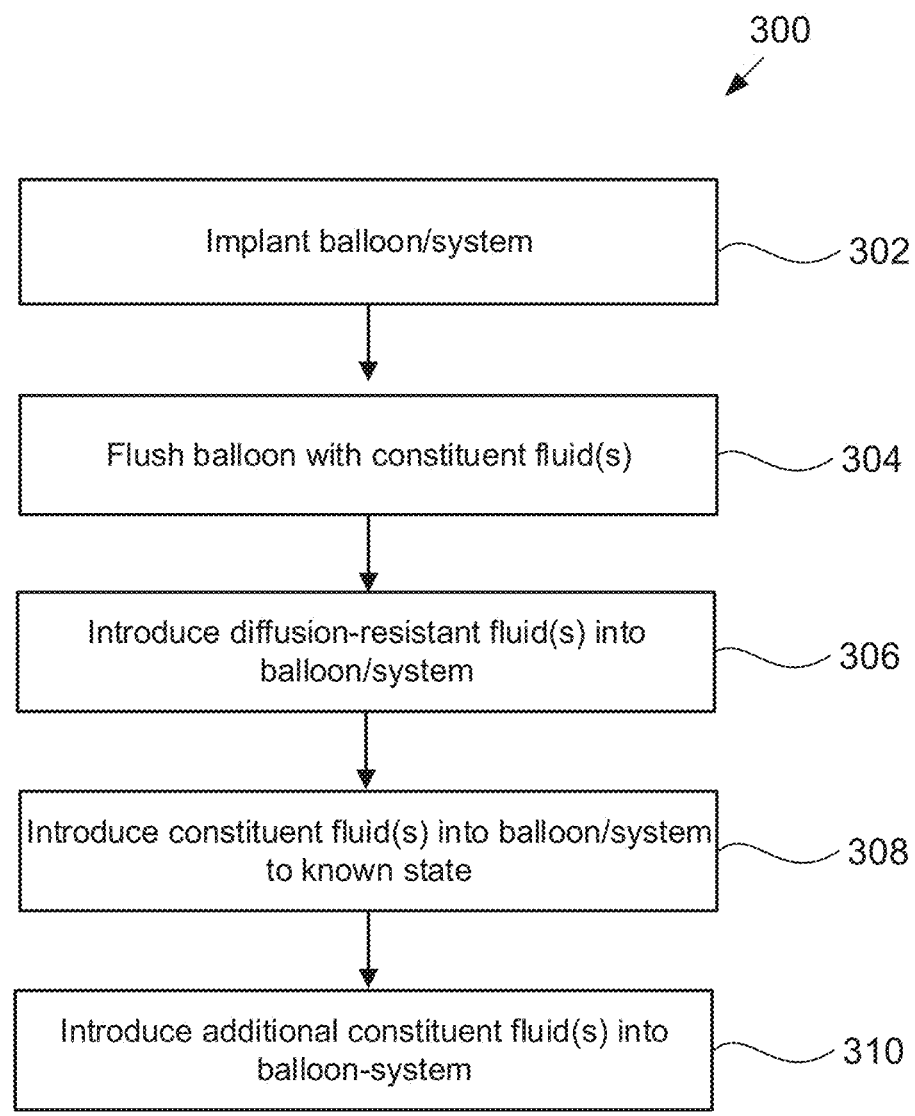
FIG. 3A is a flow chart of exemplary method steps for introducing the fluid mixture into the implantable device, in accordance with some aspects of the present disclosure.

Referring now to FIG. 3A, exemplary method 300 for introducing a fluid mixture into the implantable device is provided. At step 302, balloon 102 may be implanted within a patient's blood vessel, e.g., the pulmonary artery. Further, implantable system components may also be implanted. For example, the anchor may be implanted in the pulmonary artery (e.g., distal to bifurcation) and the conduit and reservoir fluidicly coupled to balloon 102 may also be implanted. Further exemplary details on implantation may be found, for example, in previously-incorporated U.S. Provisional Patent Application No. 63/044,337 to Harder and/or the previously-incorporated patents to Vollmers and/or Scandurra.

At step 304, balloon 102 may be flushed and/or purged with one or more constituent fluids, e.g., gases local to the patient's blood vessel including, for example, NO, He, $H_2O$, $CO_2$, $O_2$, $N_2$, Ar, and/or $CH_4$. Any gas found in the atmosphere may also be present in the blood stream at a level controlled by its partial pressure in the atmosphere, e.g., inert gases, or at a level controlled by biological processes, e.g., metabolic byproducts, or metabolically interacting gases such as CO, hydrogen sulfide, and methane, which may come from the surrounding atmosphere or from various body tissues, organs, or microbes within or on the body. For example, gas samples from sheep show approximately 1% argon which matches its atmospheric concentration, and approximately 1-3% methane, which is produce by gut microbes and released in exhaled breath. In a preferred embodiment, the one or more constituent fluids is a mixture of $O_2$, $CO_2$, and $N_2$. For example, the gas mixture may be majority $N_2$ followed by a lesser percentage of $CO_2$ and a percentage of $O_2$ less than the percentage of $CO_2$. In one example, the constituent fluids are a mixture of 7%±1% $O_2$, 12%±1% $CO_2$ and balance $N_2$.

The constituent fluid(s) may be introduced into the balloon using the conduit and/or reservoir. For example, the constituent fluid(s) may be introduced through a septum of the reservoir pierced with a needle/syringe. The balloon, conduit, and reservoir may all be implanted prior to introducing the fluids.

The balloon may be flushed with the constituent fluids one or more times. In a preferred embodiment, the balloon is flushed multiple times in step 304. The flushing step may be used to create a vacuum in the balloon and/or the implantable system (e.g., balloon, conduit, and reservoir).

Figure 4:
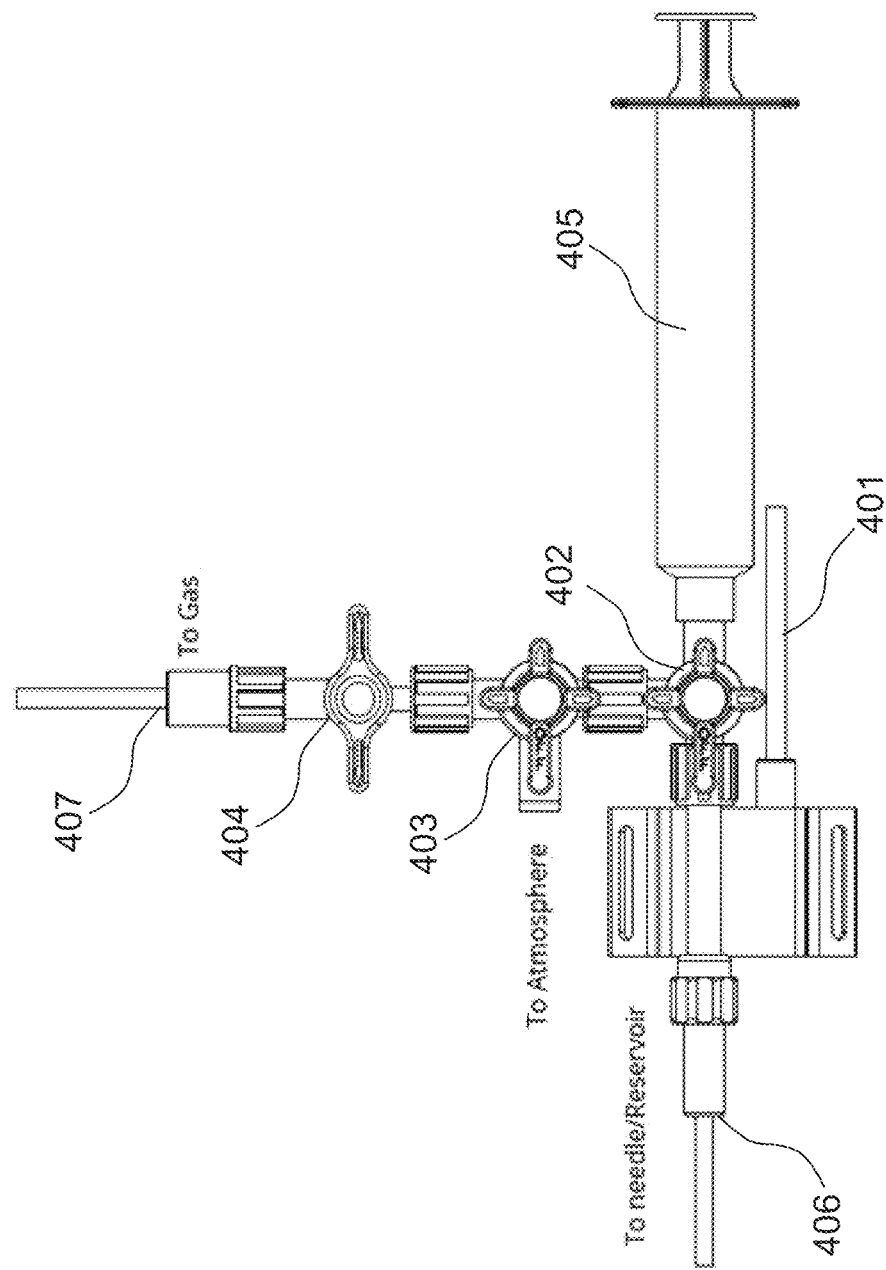
FIG. 4 illustrates an exemplary device for introducing the fluid mixture into the implantable device.

An exemplary gas purge procedure is described with reference to FIG. 4. First, reservoir 106 is examined (e.g., palpate or using ultrasound) through the skin to locate the fill port of reservoir 106, e.g., septum 112. Then, a needle (e.g., Huber needle) coupled to needle port 406 is inserted into septum 112. Next, the pressure is measured, e.g., via pressure transducer 401, and evaluated to ensure that the data acquisition system is getting a clean pressure signal from reservoir 106. One or more valves (e.g., first 3-way stopcock 402, second 3-way stopcock 403, and 1-way stopcock 404) may be opened to vent reservoir 106 to atmosphere, and the pressure signals should be verified to return to zero. Next, the one or more valves to reservoir 106 are closed and the waveform may be assessed to confirm that the mean pressure has been zeroed. Syringe 405 may be used to open reservoir 106 through, e.g., first 3-way stopcock 402, and approximately 100 ml may be drawn using syringe 405 (e.g., a 140 ml syringe) to create a vacuum within reservoir 106. The vacuum should be maintained for a time period (e.g., 10 seconds) before closing first 3-way stopcock 402 to reservoir 106. Syringe 405 may then be emptied to atmosphere through another one of the one or more valves, e.g., second 3-way stopcock 403. Next, syringe 405 may be filled with Mixed Gas, e.g., having the desired ratios of the one or more constituent fluids discussed above, from a tank with a volume of Mixed Gas (e.g., approximately 110 ml of Mixed Gas), and syringe 405 may be briefly vented to equilibrate to atmospheric pressure. For example, in some embodiments, Mixed Gas may be a mixture of $O_2$, $CO_2$, and $N_2$, e.g., 7%±1% $O_2$, 12%±1% $CO_2$ and balance $N_2$. Mixed Gas may have its highest percentage of $N_2$, followed by the next highest percentage of $CO_2$, followed by the next highest percentage of $O_2$. For example, Mixed Gas may be 7%±1% $O_2$, 12%±1% $CO_2$ and balance $N_2$. Reservoir 106 may then be opened to syringe 405 using first 3-way stopcock 402, and Mixed Gas may be added to reservoir 106 until a pressure signal is observed with a mean pressure of approximately 10 mmHg on the data acquisition system. That gas level should be maintained for a time period, e.g., approximately 15 seconds, to verify that the cardiac pressure cycles are visible on the pressure trace. First 3-way stopcock 402 to reservoir 106 may then be closed, and the remaining gas exhausted from syringe 405 to atmosphere. If reservoir 106 is unintentionally opened to atmosphere, the Gas Purge Procedure and Gas Fill procedures should be repeated. The above steps may be repeated, e.g., for a total of 7 purge and fill sequences.

Next, reservoir 106 is opened to syringe 405 using first 3-way stopcock 402 and an amount may be drawn into syringe 405, e.g., approximately 100 ml, to create a vacuum within reservoir 106. The vacuum should be maintained for a time period, e.g., 10 seconds, before first 3-way stopcock 402 to reservoir 106 is closed. Syringe 405 may be replaced with a second syringe, e.g., a 60 ml syringe, and 1-way stopcock 404, and the second syringe may be filled, e.g., to 60 ml, with Mixed Gas. The second syringe may then be vented to atmosphere and 1-way stopcock 404 connected to the second syringe may be closed. The filled second syringe and 1-way stopcock 404 may then be removed from system 100 and set aside for later. A third syringe, e.g., a second 60 ml syringe, and another 1-way stopcock 404 may be placed in the place of the previous syringe/stopcock and filled, e.g., to 60 ml, with Mixed Gas. While leaving this third Mixed Gas syringe attached, the third syringe may be vented to atmosphere and 1-way stopcock 404 connected to the third syringe may be closed. System 100 should be under vacuum and ready for gas fill, which may be verified using the data acquisition system.

Referring again to FIG. 3A, at step 306, balloon 102 may be filled with a diffusion-resistant fluid(s), e.g., a gas having a large molecular weight, having a very slow diffusion rate to offset the difference between desired reservoir pressure and total of the partial pressures of the constituent gases in the balloon. In other words, the diffusion-resistant gas has a very low permeation rate through the balloon membrane of balloon 102. In a preferred embodiment, the diffusion-resistant gas selected meets the following requirements: (1) has a diffusion rate that is slower than any of the existing gases found in the bloodstream, (2) is nontoxic and preferably inert in the conditions found in the body, and (3) remains in its gaseous phase at body temperature and has absolute pressures between 500-1000 mmHg. Accordingly, the diffusion-resistant gas should have a low boiling temperature well below body temperature. For example, the diffusion-resistant gas may be sulfur hexafluoride ($SF_6$), or a perfluorinated compound, or both. Accordingly, with the solution outlined above, the pressure and volume in system 100 will be controlled by the diffusion of $SF_6$ out of balloon 102 into the venous blood. Available data suggest that this occurs at a rate 30 times slower than $N_2$. Larger molecular fluorocarbons are undoubtedly slower and meet the requirements discussed above, and thus may also be suitable for use with system 100.

Accordingly, first, the desired amount of diffusion-resistant gas, e.g., $SF_6$, to be injected into balloon 102 must be determined. For example, the amount of diffusion-resistant gas added may be selected from 20 to 41 ml, in some examples. As shown in Table 3 below, the desired amount of diffusion resistant gas (e.g., $SF_6$) may be determined based on the patient's resting mean pulmonary arterial pressure (mPAP) and/or the altitude of the residence that the patient is expected to be at for the months following the implant filling procedure. If the altitude of the patient's residence is expected to vary over the following months following the implant filling procedure, the lower altitude value should be selected in Table 3 to determine the amount of $SF_6$ to be injected into the balloon. For example, the amount of $SF_6$ may be calculated by determining the difference between the expected partial pressures of other gases in the blood (e.g., $O_2$, $CO_2$ and $N_2$) and the pulmonary artery pressures, such that the amount of $SF_6$ calculated makes up the difference. Once the desired amount of $SF_6$ is determined, that amount of $SF_6$ may be injected into the balloon, e.g., via the reservoir, as described in the exemplary gas fill procedure described below.

TABLE 3

| Patient Area of Residence | | Milliliters (ml) of $SF_6$ | | | | | |
|---|---|---|---|---|---|---|---|
| Altitude | Avg. Local Pressure | Gas to Add to Implanted System Patient Resting mPAP (mmHg) | | | | | |
| (ft) | (Torr) | 30 | 40 | 50 | 60 | 70 | 80 |
| 0 | 760.0 | 21.1 | 23.4 | 25.6 | 27.7 | 29.8 | 31.9 |
| 1000 | 729.6 | 22.0 | 24.3 | 26.6 | 28.8 | 30.9 | 33.1 |
| 2000 | 706.8 | 22.7 | 25.1 | 27.4 | 29.6 | 31.9 | 34.0 |
| 3000 | 684.0 | 23.4 | 25.8 | 28.2 | 30.6 | 32.8 | 35.0 |
| 4000 | 653.6 | 24.4 | 27.0 | 29.5 | 31.9 | 34.2 | 36.5 |
| 5000 | 630.8 | 25.3 | 27.9 | 30.4 | 32.9 | 35.3 | 37.6 |
| 6000 | 608.0 | 26.2 | 28.9 | 31.5 | 34.0 | 36.5 | 38.9 |
| 7000 | 585.2 | 27.1 | 29.9 | 32.6 | 35.2 | 37.8 | 40.2 |

Referring again to FIG. 4, an exemplary gas fill procedure is described. 1-way stopcock 404 to the Mixed Gas tank and the Mixed Gas tank regulator may be closed, and the Mixed Gas tank may be removed from system 100 and replaced with an $SF_6$ compressed gas tank. Gas line 407 may then be purged with $SF_6$ to the open port, e.g., a Luer port, on second 3-way stopcock 403, and a fourth syringe, e.g., a third 60 ml syringe, may be attached to the open Luer port of second 3-way stopcock 403. Next, the fourth syringe may be filled with the chosen volume of $SF_6$ and vented to relieve pressure by removing gas line 407 and 1-way stopcock 404 to the gas tank. A non-vented style cap may be placed over the open Luer port on second 3-way stopcock 404. The fourth syringe filled with $SF_6$ may then be opened to reservoir 106 through first and second 3-way stopcocks 402, 403, and the chosen $SF_6$ syringe volume may be injected into reservoir 106. Next, the second 3-way stopcock is closed to first 3-way stopcock 402

Referring again to FIG. 3A, at step 308, the constituent fluid(s) are introduced into balloon 102 and/or system 100 to a known state. For example, Mixed Gas may be introduced until the pressure and/or volume of fluids within balloon 102 and/or system 100 reaches a known state. In a preferred embodiment, the pressure within the balloon and/or system is increased from vacuum to a target pressure range. For example, the pressure may be increased to a predetermined range around atmospheric pressure (e.g., 0±0.5 mmHg).

Referring again to FIG. 4, reservoir 106 may be opened to the third syringe filled with Mixed Gas through first 3-way stopcock 402, and 1-way stopcock 404 attached to the third syringe is opened to first 3-way stopcock 402. The pressure of system 100 may be brought up so that the pressure offset equals 0±0.5 mmHg by adding Mixed Gas from the third syringe to the known state. After a time period, e.g., preferably 10 seconds, reservoir 106 is then vented to atmosphere by removing the third syringe and the attached 1-way stopcock 404 (the third syringe will no longer be used and may be discarded), and first 3-way stopcock 402 may be turned off to open port.

Referring again to FIG. 3A, at step 310, balloon 102 may be filled with additional Mixed Gas, e.g., one or more constituent fluids. Accordingly, the desired amount of Mixed Gas to be introduced into balloon 102 must be determined. For example, the amount of local constituent fluids added may be selected from 16 to 36 ml, in some examples. As shown in Table 4 below, the desired amount of constituent fluids may be determined based on the patient's resting mean pulmonary arterial pressure (mPAP) as well as the altitude of the residence that the patient is expected to be at for the months following the implant filling procedure. If the altitude of the patient's residence is expected to vary over the following months following the implant filling procedure, the lower altitude value should be selected in Table 4 to determine the amount of constituent fluids to be injected into the balloon. Once the desired amount of the constituent fluids is determined, that amount of constituent fluids may be injected into balloon 102, e.g., via septum 112 of reservoir 106, at step 310.

For example, the remaining second syringe filled with Mixed Gas may be adjusted, e.g., to the volume obtained from Table 4 above, and 1-way stopcock 404 may be attached to the open port of first 3-way stopcock 402. Reservoir 106 may then be opened to the second syringe filled with Mixed Gas through first 3-way stopcock 402 and 1-way stopcock 404, and the volume of Mixed Gas (obtained from Table 4) contained in the second syringe may be injected into reservoir 106. The pressure may be verified on the data acquisition system as necessary. Finally, first 3-way stopcock 402 is shut off to reservoir 106 and the needle may be removed from septum 112. As will be understood by a person ordinarily skilled in the art, steps 308 and step 310 may be conducted in one step.

TABLE 4

| Patient Area of Residence | | Milliliters (ml) of Local Gases | | | | | |
|---|---|---|---|---|---|---|---|
| Altitude | Avg. Local Pressure | to Add to Implanted System Patient Resting mPAP (mmHg) | | | | | |
| (ft) | (Torr) | 30 | 40 | 50 | 60 | 70 | 80 |
| 0 | 760.0 | 16.96 | 19.46 | 21.96 | 24.46 | 26.96 | 29.46 |
| 1000 | 729.6 | 17.27 | 19.88 | 22.48 | 25.09 | 27.69 | 30.30 |
| 2000 | 706.8 | 17.52 | 20.21 | 22.90 | 25.59 | 28.28 | 30.97 |
| 3000 | 684.0 | 17.79 | 20.57 | 23.35 | 26.13 | 28.91 | 31.69 |
| 4000 | 653.6 | 18.18 | 21.09 | 24.00 | 26.91 | 29.81 | 32.72 |
| 5000 | 630.8 | 18.49 | 21.51 | 24.52 | 27.54 | 30.55 | 33.56 |
| 6000 | 608.0 | 18.83 | 21.96 | 25.09 | 28.21 | 31.34 | 34.47 |
| 7000 | 585.2 | 19.20 | 22.45 | 25.70 | 28.95 | 32.19 | 35.44 |

Accordingly, diffusion-resistant gas, e.g., $SF_6$, and the one or more constituent fluids, e.g., NO, He, $H_2O$, $CO_2$, $O_2$, $N_2$, Ar, or $CH_4$, within balloon 102 are permitted to equilibrate across balloon 102 according to their respective partial pressure gradients across the membrane of balloon 102. Over time, e.g., after 30 days, the fluids will equalize across balloon 102 such that the composition of fluids within balloon 102 will match the partial pressures of venous gases. For example, the amount of one or more constituent fluids within balloon 102 will correspond with the partial pressures of the respective gases within the venous blood, as the fluids equalize across balloon 102. However, as described above, $SF_6$ diffuses much slower than the other constituent fluids, and thus, after, e.g., 30 days post-filling balloon 102, the amount of $SF_6$ within balloon 102 will still be very close to the initial filling amount.

Figure 3B:
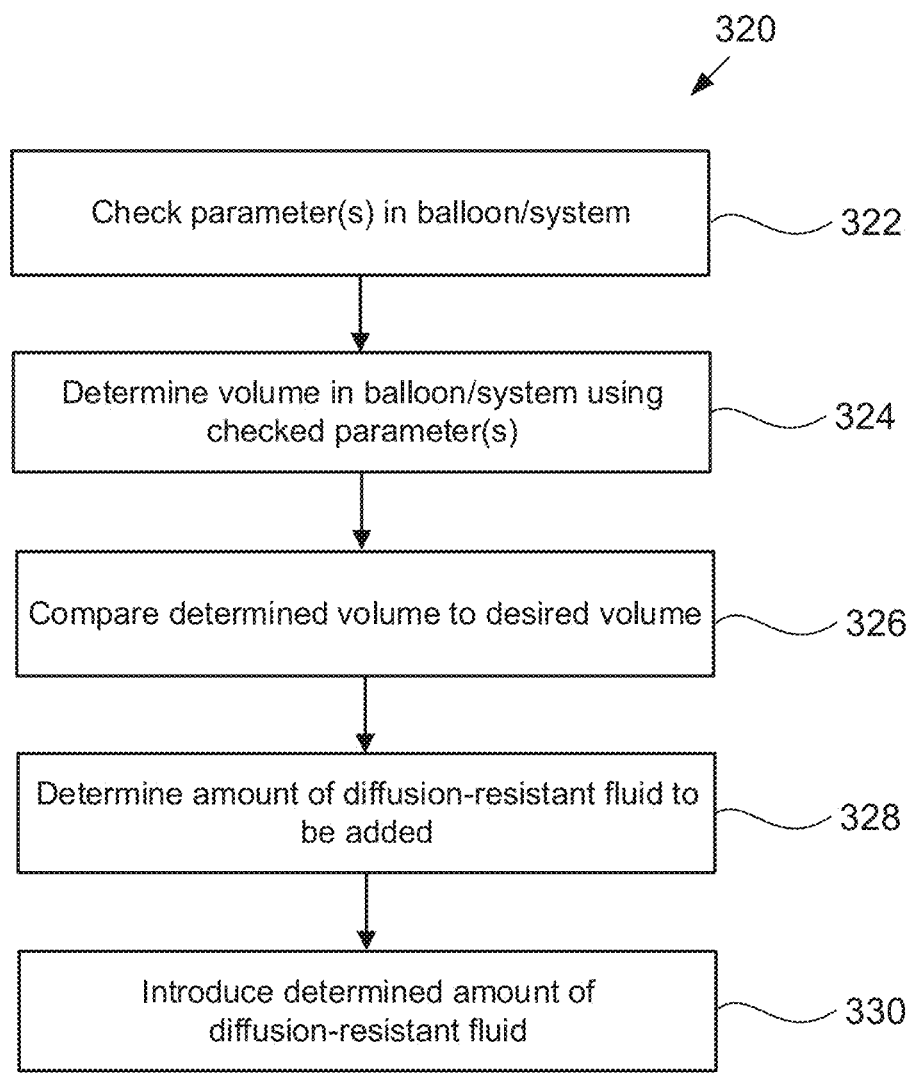
FIG. 3B is a flow chart of exemplary method steps for refilling/checking/adjusting fluid within the implantable device, in accordance with some aspects of the present disclosure.

As the fluids within balloon 102 may diffuse out of balloon 102 over time and/or fluids from the patient's vasculature may diffuse into balloon 102 over time, a refill/extraction procedure to adjust the amount of diffusion-resistant gas within balloon 102 may be conducted at a time following the initial implant filling procedure of method 300, as described in further detail with regard to FIG. 3B.

Prior to the refill/extraction procedure, an optional liquid extraction procedure may be conducted on balloon 102/system 100 to remove unwanted liquid, e.g., water vapor, that has accumulated within balloon 102. The liquid extraction procedure, and structure for the same, are described in the previously-incorporated Harder patent application. In some examples, first, with the patient laying in a recumbent position, reservoir 106 is examined to locate the fill port (this may be assisted with echo or skin tattoos as needed), e.g., septum 112. The area may be prepped per the recommended sterile procedures. Next, a pressure sensor, e.g., a Utah Medical Products DPT-100, may be attached to a needle, e.g., a 22-gauge Huber style non-coring needle of appropriate length. A 3-way stopcock may be attached on the back side of the pressure sensor, and a syringe, e.g., a 25 ml syringe, may be attached to the open port on the 3-way stopcock. The third port should be capped to prevent system venting. The pressure sensor may then be attached to a hemodynamic monitor or data acquisition (DAQ) system and zeroed. Using proper sterile technique, the needle is inserted through the skin and septum 112 of reservoir 106, and advanced until a clear pulmonary artery pressure shape signal is observed on the monitor. Once a signal has been obtained, the patient should be instructed to turn so the reservoir is laying perpendicular to the table (this causes any moisture condensed in reservoir 106 to pool around the gas access). Gas/liquid may then be withdrawn into the syringe until no more can be withdrawn. The syringe may then be tilted to return any extracted gas to system 100, and the volume of liquid removed from system 100 should be recorded. Next, the gas check/refill procedure may be performed as described in further detail below with regard to FIG. 3B.

Referring now to FIG. 3B, during gas check/refill procedure 320, the current active volume of fluids, e.g., the diffusion-resistant gas and the constituent fluids, within balloon 102 may be measured to determine the amount of diffusion-resistant gas, e.g., $SF_6$, that should be injected into balloon 102 to achieve a desired active volume of fluids within balloon 102, or the amount of fluids within balloon 102 that should be extracted to achieve the desired active volume of fluids within balloon 102. As shown in FIG. 3B, at step 322 of refill/extraction procedure 320, the clinician may check one or more parameters of balloon 102/system 100.

For example, first, with the patient laying in a recumbent position, reservoir 106 is examined to locate the fill port (this may be assisted with echo or skin tattoos as needed), e.g., septum 112. The area may be prepped per the recommended sterile procedures. Next, a pressure sensor, e.g., a Utah Medical Products DPT-100, may be attached to a needle, e.g., a 22-gauge Huber style non-coring needle of appropriate length. A 3-way stopcock may be attached on the back side of the pressure sensor, and a syringe, e.g., a 25 ml syringe, may be attached to the open port on the 3-way stopcock. The third port of the 3-way stopcock should be capped to prevent system venting. The pressure sensor may then be attached to a hemodynamic monitor or data acquisition (DAQ) system and zeroed. Using proper sterile technique, the needle is inserted through the skin and septum 112 of reservoir 106, and advanced until a clear pulmonary artery pressure shape signal is observed on the monitor. Once a signal has been obtained, gas may be withdrawn into the syringe in predetermined increments, with a pause, e.g., preferably a 10 second pause, after every volume adjustment before the stopcock is closed to the pressure sensor. The withdrawn volume and mean value of the pressure signal should be recorded. As the mean pressure approaches zero, the increment size should be reduced, e.g., to 0.5 or 1 ml. Withdrawal of the volume should be continued until the mean pressure becomes negative.

At step 324, the volume of fluids within balloon 102/system 100 may be determined using the checked parameters. For example, the zero-crossing volume (this is the current active volume of the balloon) may be estimated or extrapolated from the checked parameters at step 324, and the difference between the current active volume and the desired active volume may be determined at step 326 by comparing the measured current active volume with the desired active volume of balloon 102/system 100.

At step 328, the amount of diffusion-resistant gas that should be introduced into (or extracted from) balloon 102/system 100 may be determined. The amount of diffusion-resistant gas may be determined based on a percentage of desired volume to add to balloon 102/system 100. In some examples, the amount is based on mPAP and/or altitude. The amount may be determined from a table, such as Table 5 below. For example, if the current active volume is below the desired active volume of fluids within balloon 102, the amount of $SF_6$ to be injected into balloon 102 may be determined from Table 5 below. In some examples, the amount of diffusion-resistant gas to add is based on the calculated difference from step 326. The percent of diffusion-resistant gas of the desired active volume to add to the implant during a refill may be a percentage of the desired increase, and is preferably selected from 10-25%. For example, the added volume of diffusion-resistant fluid plus the current volume of fluid within the system may be less than the desired volume within the system at the end of the procedure. However, the selected volume of diffusion-resistant fluid will cause an infusion of fluid from the body into the implantable system to reach the desired volume over time (e.g., within hours or days or weeks). The added amount of $SF_6$ will dilute the other constituent fluids and reduce their partial pressures, thereby causing an influx of the other constituent fluids into the system that will make up the remaining fraction of the desired volume.

For example, according to Table 5, if the patient's mPAP is 30 mmHg, and the patient is at sea level (0 ft altitude), an amount of $SF_6$ equal to 10% of the amount of fluid that should be added to balloon 102 so that the current active volume of system 100 equals the desired active volume, should be injected into system 100. At step 330, the determined amount of diffusion-resistant fluid is introduced into (or extracted from) balloon 102/system 100. Thus, if it is determined at step 328 that 10 ml of fluid must be added to achieve the desired active volume, 1 ml of $SF_6$ should be added at step 330. The 1 ml of $SF_6$ added to balloon 102 will cause a reduction of partial pressures of the one or more constituent fluids of the Mixed Gas within system 100, thereby causing an influx of the constituent fluids into system 100 from the surrounding vasculature over time, e.g., a total of 9 ml influx of constituent fluids. Accordingly, an addition of 1 ml of $SF_6$ at step 330 ultimately results in a net increase of 10 ml over time, such that the desired active volume is achieved. At step 330, the determined amount of diffusion-resistant fluid may be introduced alone or may be introduced with additional fluid(s) (e.g., the constituent fluid(s)). For example, when introduced with additional fluid(s), a mixture of the constituent fluid(s) with the diffusion-resistant fluid may be used, e.g., using the percentages from Table 5 below. The mixture may be introduced to reach a predetermined state using feedback based on sensed parameters of the patient's physiology and/or sensed parameters within the implanted system (e.g., when reservoir pulse pressure has peaked and/or begins to decline, and/or the diastolic pressure increases at a predetermined rate) as described in further detail below.

Thus, if the desired volume is greater than the current active volume, the calculated amount of $SF_6$ may be drawn into the 25 ml syringe. The cap may then be removed from the 3-way stopcock and the syringe filled with $SF_6$ may be connected to the side port of the 3-way stopcock. At step 330, the determined amount of diffusion-resistant fluid, e.g., $SF_6$ volume, may be injected into reservoir 106 and the 3-way stopcock may be shut off to the $SF_6$ syringe. Finally, the remaining extracted volume may be returned to reservoir 106 and the stopcock may be closed to reservoir 106. If needed, a liquid extraction may be performed as described above.

TABLE 5

| Patient Area of Residence | | $SF_6$ percent (%) of Desired Active Volume to Add to the Implanted System during Refill Procedure Patient Resting mPAP (mmHg) | | | | | |
|---|---|---|---|---|---|---|---|
| Altitude (ft) | Avg. Local Pressure (Torr) | 30 | 40 | 50 | 60 | 70 | 80 |
| 0 | 760.0 | 10% | 12% | 13% | 14% | 15% | 16% |
| 1000 | 729.6 | 11% | 13% | 13% | 14% | 15% | 16% |
| 2000 | 706.8 | 11% | 12% | 14% | 15% | 16% | 17% |
| 3000 | 684.0 | 12% | 13% | 14% | 15% | 16% | 17% |
| 4000 | 653.6 | 12% | 13% | 15% | 16% | 17% | 18% |
| 5000 | 630.8 | 13% | 14% | 15% | 16% | 18% | 19% |
| 6000 | 608.0 | 13% | 14% | 16% | 17% | 18% | 19% |
| 7000 | 585.2 | 13% | 15% | 16% | 17% | 19% | 20% |

If the current active volume is above the desired active volume of fluids within balloon 102, an amount of fluid within balloon 102 may be extracted until the desired active volume of fluids within balloon 102 is achieved. For example, the amount of unwanted volume may be expelled from the syringe through the 3-way stopcock (reservoir 106 should not be vented to atmosphere), and the remaining volume may be returned to reservoir 106 and the needle may be removed.

In one embodiment, at step 330, the determined amount of diffusion-resistant fluid may be introduced with additional fluid(s) (e.g., the constituent fluid(s)). Accordingly, after the volume of fluids within balloon 102/system 100 is determined at step 324 based on the volume of fluids withdrawn from balloon 102/system 100 and the checked parameters (until the mean pressure becomes negative), the fluids withdrawn from balloon 102/system 100 may be returned to balloon 102/system 100 until a predetermined state is reached while observing the checked parameters. For example, small incremental amounts of the withdrawn fluids may be re-introduced into system 100/balloon 102/reservoir 106 while reservoir pulse pressure and/or diastolic pressure is observed. As the constituent fluids/diffusion-resistant gas mixture is injected into reservoir 106, reservoir pulse pressure will increase, peak, and then begin to decline. At the same time, diastolic pressure will begin to increase quickly. The preferred balloon fill is achieved at the point when measurable parameter(s) reach a predetermined state (e.g., reservoir pulse pressure has peaked and/or begins to decline, and/or the diastolic pressure increases quickly). Once the preferred balloon fill is achieved, no more of the withdrawn fluids should be added to system 100/balloon 102/reservoir 106.

If all of the withdrawn fluids has been returned to system 100/balloon 102/reservoir 106, and the monitored parameters indicate that more fluid should be added to system 100/balloon 102/reservoir 106 to achieve the preferred balloon fill, an amount of diffusion-resistant gas to be added may be determined, e.g., based on Table 5. For example, an amount of the constituent fluids may be mixed with an amount of diffusion-resistant gas to form a fluid mixture having the desired percentage of the diffusion-resistant fluid, e.g., based on historical or current mPAP patient data and/or altitude in accordance with Table 5. For example, according to Table 5, for a patient's with mPAP of 30 mmHg at sea level (0 ft altitude), the amount of fluid mixture that should be added to system 100/balloon 102/reservoir 106 so that the current active volume of system 100 equals the desired active volume should have 10% $SF_6$. Accordingly, a 10 ml fluid mixture should have 1 ml $SF_6$ and 9 ml constituent fluids, e.g., Mixed Gas. The fluid mixture having constituent fluids and diffusion-resistant fluid may then be introduced incrementally into system 100/balloon 102/reservoir 106 while observing the checked parameters. Once the preferred balloon fill is achieved, as indicated by reservoir pulse pressure and/or diastolic pressure as described above, no more of the fluid mixture should be added to system 100/balloon 102/reservoir 106.

Gas check/refill procedure 300 may be conducted after a predetermined time following the initial filling of balloon 102, e.g., 30 days. Accordingly, gas check/refill procedure 300 may be repeated at irregular or regular intervals, e.g., weekly, monthly, bi-monthly, 30 days after initial filling of balloon 102, then 60 days after initial filling of balloon 102, then every 90 days after the first 60 days after initial filling of balloon 102.

After the gas check/refill procedure, balloon 102 having the equalized constituent fluids and the diffusion-resistant gas therein, may transition between the expanded state and the collapsed state responsive to pressure fluctuations in the blood vessel while reducing permeation of fluids across balloon 102 throughout multiple cardiac cycles. Alternatively, balloon 102 may be initially injected with a composition of one or more local gases, such that the partial pressures of the one or more local gases are permitted to equilibrate across balloon 102 according to their respective partial pressure gradients across the membrane of balloon 102 for a period of time after the initial filling procedure, prior to injecting balloon 102 with the desired volume of the diffusion-resistant gas, as described in further detail below.

Figure 5:
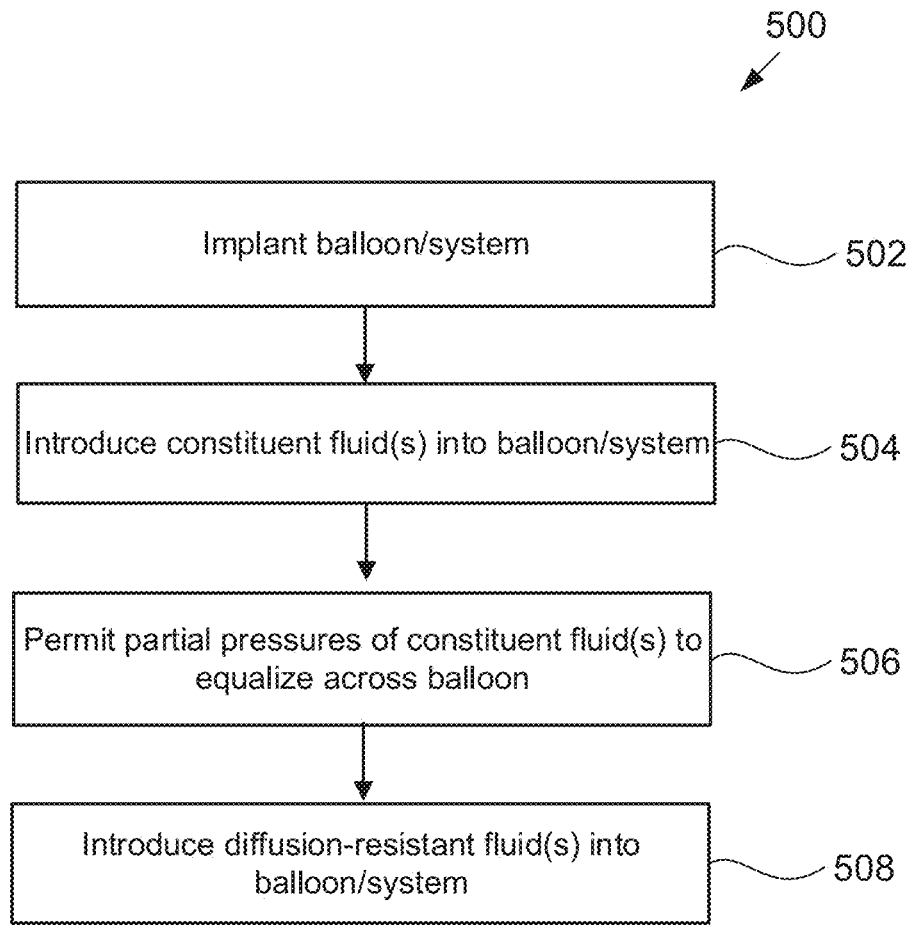
FIG. 5 is a flow chart of alternative exemplary method steps for introducing the fluid mixture into the implantable device in accordance with some aspects of the present disclosure.
Figure 6A:
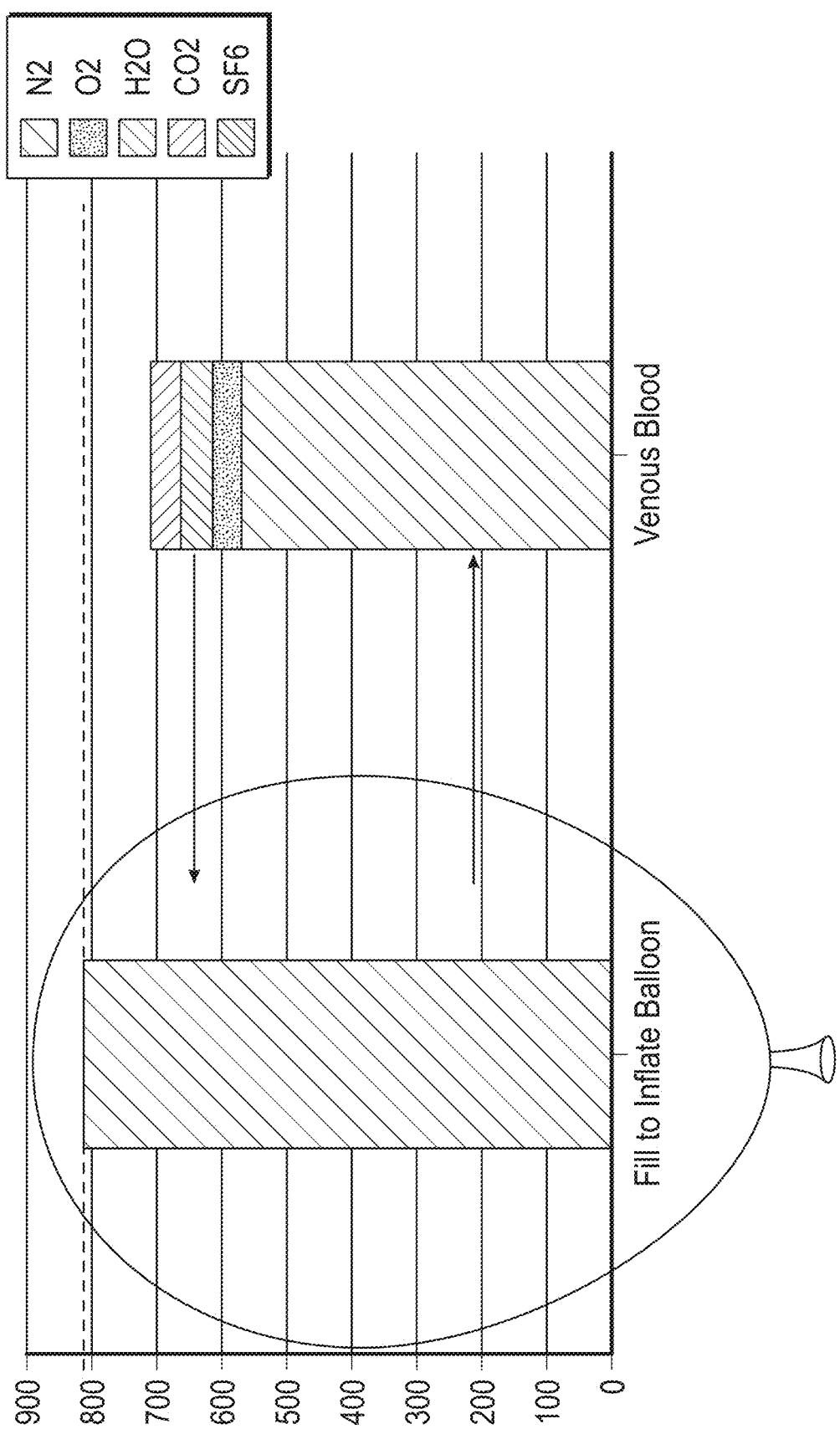
FIGS. 6A-6D illustrate steps taken during the method of FIG. 5, according to some embodiments of the present invention.

In accordance with another aspect of the present invention, referring now to FIG. 5, another exemplary method 500 for introducing fluids into an implantable system is provided. Some of the steps of method 500 may be further elaborated by referring to FIGS. 6A-6D. The balloon illustrated in FIGS. 6A-6D is not to scale, and only shown to distinguish the one or more constituent fluids, e.g., gases, that are within the balloon at any given time. At step 502, balloon 102 may be implanted within a patient's blood vessel, e.g., the pulmonary artery, as described above. At step 504, balloon 102 may be filled with Mixed Gas as described above with regard to FIG. 3A, e.g., one or more constituent fluids local to the patient's blood vessel including, for example, NO, He, $H_2O$, $CO_2$, $O_2$, $N_2$, Ar, or $CH_4$. For example, balloon 102 may be injected with the Mixed Gas via septum 112 of reservoir 106. As shown in FIG. 6A, balloon 102 may be inflated with a volume of $N_2$, such that balloon 102 has a desired pressure.

Figure 6B:
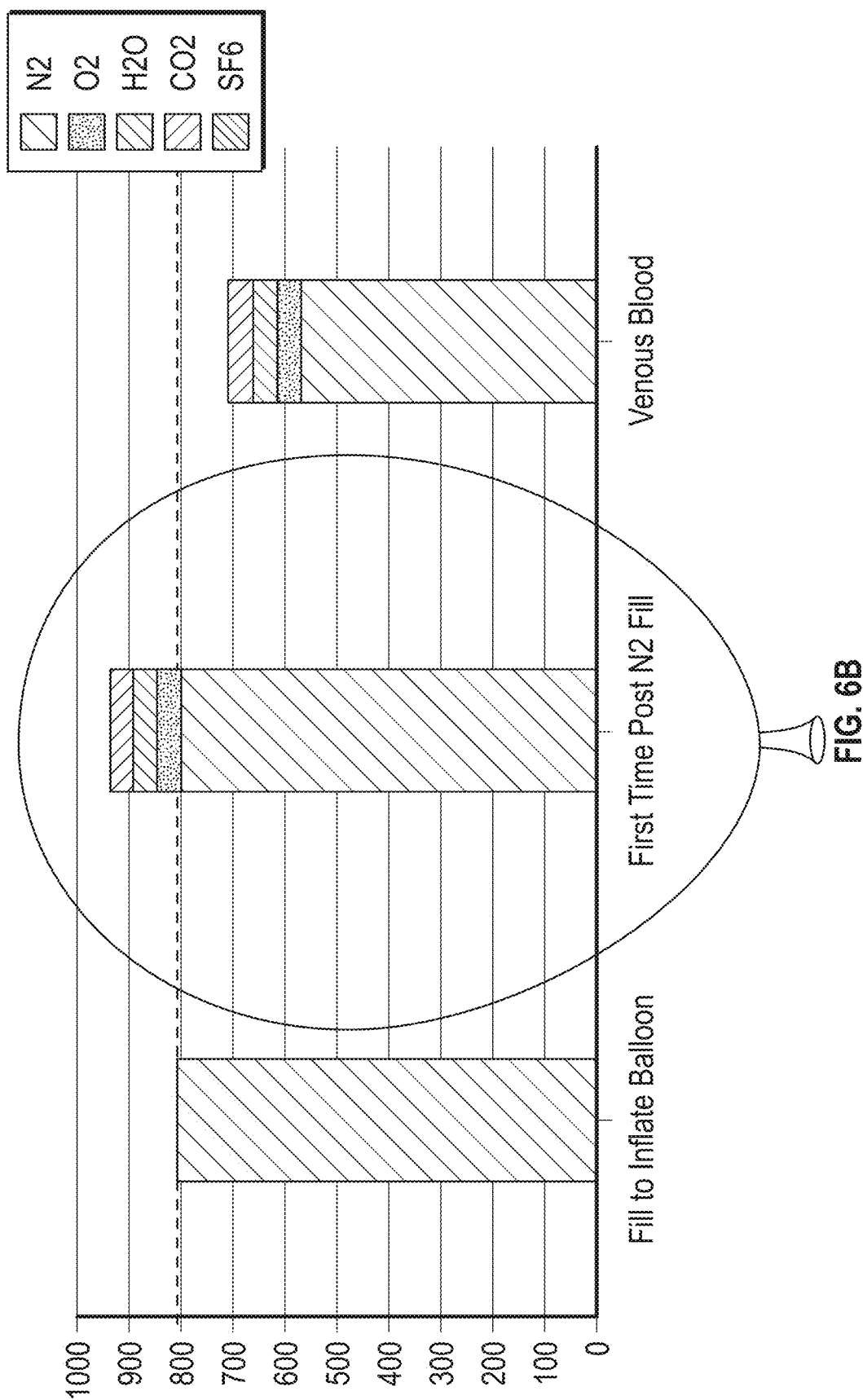

At step 506, the one or more constituent fluids, e.g., $N_2$, within balloon 102 is permitted to equilibrate across balloon 102 according to their respective partial pressure gradients across the membrane of balloon 102. In addition, as there is no amount of $H_2O$, $CO_2$, and $O_2$ initially within balloon 102, $H_2O$, $CO_2$, and $O_2$ present in the venous blood, within which balloon 102 is implanted, will infuse into balloon 102 over time until they are equalized across balloon 102. As shown in FIG. 6B, after a first time, e.g., 7 days after initial filling of balloon 102 with $N_2$, balloon 102 will contain $N_2$, as well as $H_2O$, $CO_2$, and 02. The amount of $H_2O$, $CO_2$, and $O_2$ within balloon 102 will correspond with the partial pressures of the respective gases within the venous blood, as the gases equalize across balloon 102. As described above, $N_2$ is the slowest diffuser of the four gases, and thus, after the first time post-filling balloon 102 with $N_2$, the amount of $N_2$ within balloon 102 will still be close, or slightly less, than the initial filling amount. Accordingly, balloon 102 will have an initial influx of gases, thereby causing balloon 102 to be more pressurized than desired.

Figure 6C:
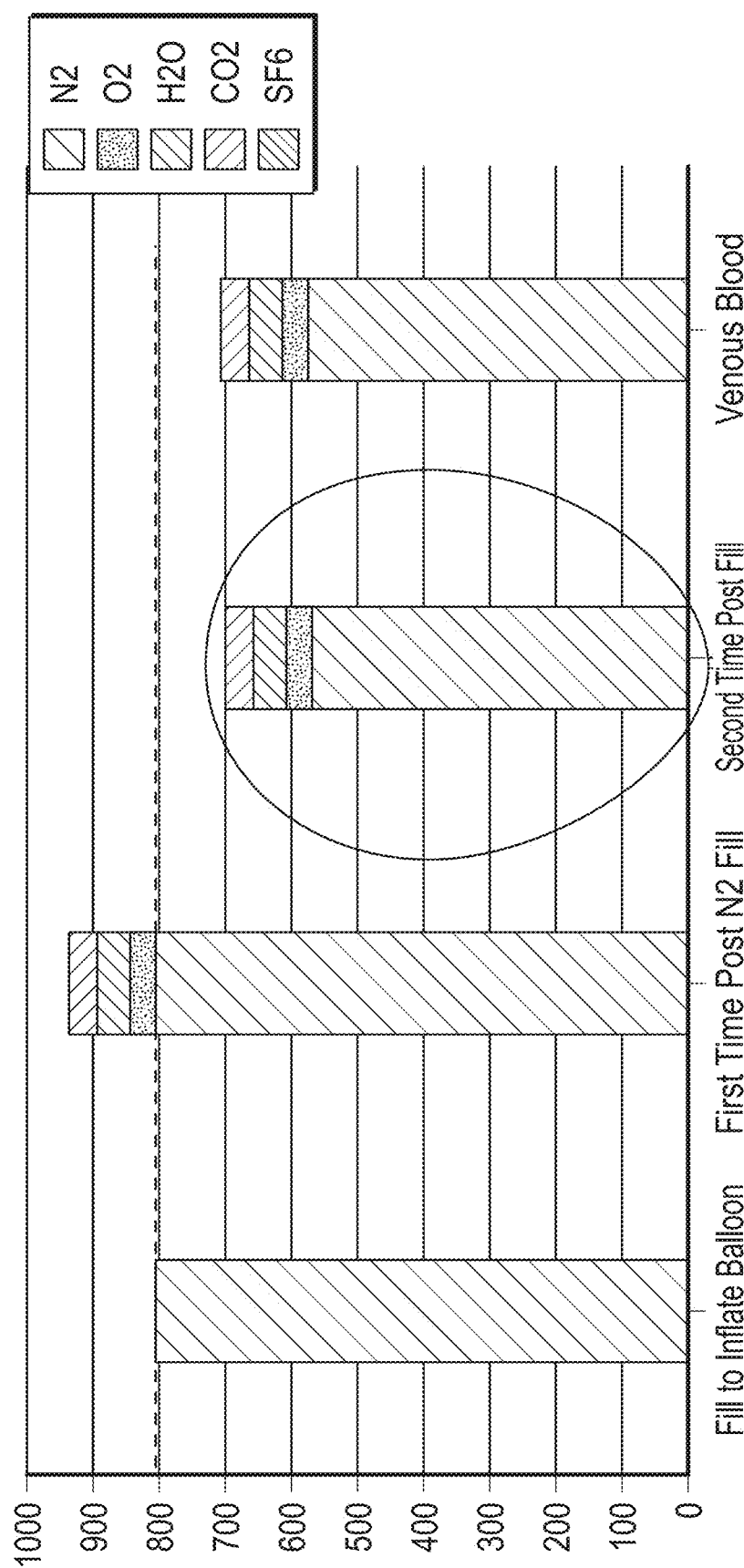

$N_2$ will eventually diffuse out of balloon 102 into the patient's blood vessel to match with the partial pressure of $N_2$ within the blood vessel. FIG. 6C illustrates balloon 102 after a second time, e.g., 30 days after the initial filling of balloon 102 with $N_2$. As illustrated in FIG. 6C, the composition of fluids within balloon 102 approximately matches the partial pressures of the local gases in the venous blood within 30 days, and accordingly, the pressure of gases within balloon 102 is less than the desired reservoir pressure. As will be understood by a person having ordinary skill in the art, balloon 102 may initially be filled with not only $N_2$, but any combination of local gases, e.g., NO, He, $H_2O$, $CO_2$, $O_2$, $N_2$, Ar, and $CH_4$, to achieve equilibrium across the balloon within the blood vessel. Over time, the gases will equalize across balloon 102 such that the composition of fluids within balloon 102 will match the partial pressures of venous gases, as shown in FIG. 6C.

Figure 6D:
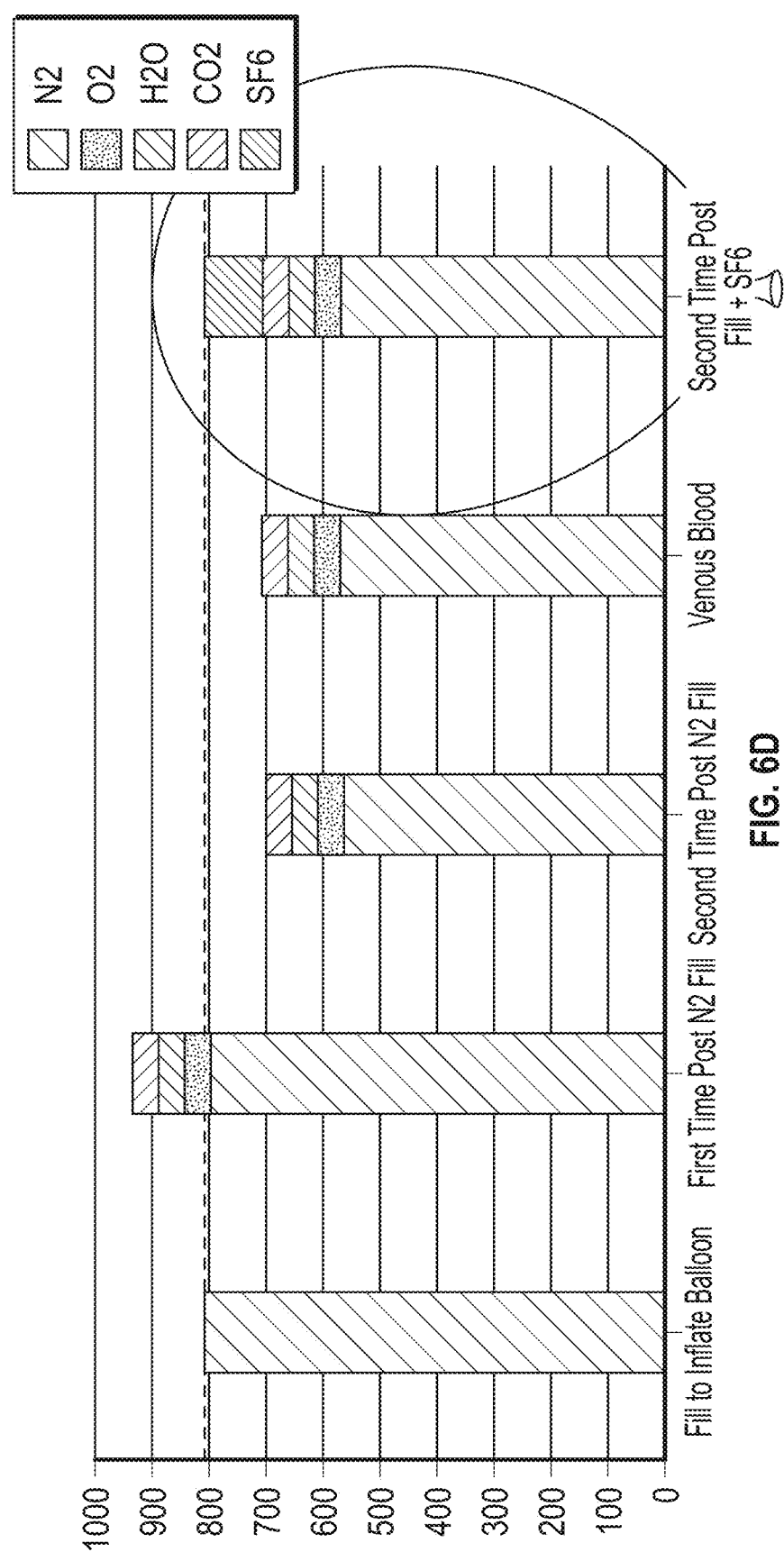

Balloon 102 could be repeatedly topped off with more of the one or more fluids already present in balloon 102, but they will eventually diffuse out of balloon 102 to equalize with the partial pressures of the venous gas. Thus, in accordance with the principles of the present invention, at step 508, balloon 102 may be filled with a diffusion-resistant gas, e.g., $SF_6$. For example, balloon 102 may be injected with a desired volume of the diffusion-resistant gas after the second time when the composition of local gases within balloon 102 have equalized across balloon 102 with the venous blood, e.g., after approximately 30 days after the initial filling of balloon 102, as shown in FIG. 6D. The amount of diffusion-resistant gas to be added to balloon 102 may be determined similar to step 328 of FIG. 3A.

As will be understood by a person having ordinary skill in the art, the time at which the plurality of local gases equalize with the partial pressures of the venous blood will depend on the initial composition of one or more constituent fluids injected within balloon 102, and the diffusion-resistant gas may be injected into balloon 102 at that time. For example, the plurality of local gases may equalize with the partial pressures of the venous blood within a predetermined amount of time (e.g., a week) of the initial filling of balloon 102, and thus the diffusion-resistant gas may be injected into balloon 102 at least the predetermined amount of time after the initial filling.

When determining the amount of the diffusion-resistant gas to inject into balloon 102, calculations may be performed with regard to partial pressures and then converted back and forth to gas volumes within the system. For example, the partial pressure of a gas divided by the total pressure of the system gives a percent of the total pressure represented by that gas. This percent also reflects the percent of volume that the gas of interest occupies in the system. For example, balloon 102 may be injected with an amount of the diffusion-resistant gas such that the diffusion-resistant gas makes up between 8-25% of the total gas mixture within balloon 102, e.g., the plurality of local gases and the diffusion-resistant gas. Balloon 102 having the equalized constituent fluids and the diffusion-resistant gas therein, transitions between the expanded state and the collapsed state responsive to pressure fluctuations in the blood vessel while reducing permeation of gases across balloon 102 throughout multiple cardiac cycles, as described in the Scandurra, Vollmers, and Harder patents/applications.

Moreover, the principles of the present invention may be utilized with other gas-filled cavities implanted in the patient's body such as valve spacers, tissue expanders, or compliance chambers. Additionally or alternatively, a small dose of the diffusion-resistant gas may be administered to natural body cavities to cause them to fill with gas, which would be useful in a variety of situations. For example, a small amount of $SF_6$ may be injected into a sinus of a patient with chronic sinus occluded with liquid. This would create a gas cavity of $SF_6$, which would in turn gather other gases from the surrounding tissue and expand the size of the gas bubble, thereby displacing liquid from the ear. Once the $SF_6$ is absorbed by the body or escapes through the natural sinus passages, the gaseous cavity expansion effect would cease. Thus, this could be used when a patient's tympanic cavity (middle ear) is filled with fluid. A small amount of the diffusion-resistant gas would slowly gather gas from the surrounding tissue and potentially force out the fluid through the Eustachian tube. In addition, a self-inflating tissue expander could utilize the principles of the present invention in the same way. For example, by creating a highly diffusion-resistant "balloon," a small amount of $SF_6$ would begin gathering gases from the surrounding tissue over an extended period of time in a slow and controllable rate.

While various illustrative embodiments of the invention are described above, it will be apparent to one skilled in the art that various changes and modifications may be made herein without departing from the invention. It will further be appreciated that the systems and methods described herein may be utilized for reducing pulsatile pressure and improving vessel compliance in blood vessels other than the pulmonary artery, and may be utilized for other medical applications as described above. The appended claims are intended to cover all such changes and modifications that fall within the true spirit and scope of the invention.

What is claimed:
1. A method for introducing fluids into an implantable system, the method comprising:
   implanting a balloon within a blood vessel of a patient;
   determining an amount of a diffusion-resistant fluid to introduce into the balloon and introducing the amount of the diffusion-resistant fluid into the balloon;

determining an amount of one or more constituent fluids to introduce into the balloon and introducing the amount of the one or more constituent fluids into the balloon;

permitting the one or more constituent fluids to equilibrate across the balloon such that each of the one or more constituent fluids is pressurized within the balloon to match their respective partial pressure in the blood surrounding the balloon within the blood vessel; and after a predetermined time period, determining a current volume of fluids within the balloon and either extracting fluids from the balloon or introducing an additional amount of the diffusion-resistant fluid into the balloon to achieve a desired active volume of fluids within the balloon.

2. The method of claim 1, wherein implanting the balloon comprises implanting the balloon within the patient's pulmonary artery.

3. The method of claim 1, wherein the diffusion-resistant fluid comprises a partial pressure equal to a difference between partial pressures of the one or more constituent fluids and a predetermined desired balloon pressure.

4. The method of claim 1, wherein a mixture of the one or more constituent fluids, prior to mixing with the diffusion-resistant fluid, consists of 7%±1% $O_2$, 12%±1% $CO_2$ and balance $N_2$.

5. The method of claim 1, wherein the diffusion-resistant fluid is sulfur hexafluoride.

6. The method of claim 1, wherein the one or more constituent fluids comprise at least one of NO, He, $H_2O$, $CO_2$, $O_2$, $N_2$, Ar, or $CH_4$.

7. The method of claim 1, wherein introducing the amount of the one or more constituent fluids into the balloon comprises:

introducing an initial amount of the one or more constituent fluids to reach a known state within the balloon; and introducing an additional amount of the one or more constituent fluids into the balloon.

8. The method of claim 1, wherein achieving the desired active volume of fluids within the balloon comprises extracting fluids from the balloon if the current volume of fluids within the balloon is greater than the desired active volume of fluids within the balloon.

9. The method of claim 1, wherein achieving the desired active volume of fluids within the balloon comprises introducing the additional amount of diffusion-resistant fluid into the balloon if the current volume of fluids within the balloon is less than the desired active volume of fluids within the balloon.

10. The method of claim 9, wherein introducing the additional amount of diffusion-resistant fluid into the balloon comprises determining the additional amount of diffusion-resistant fluid into the balloon based on at least one of the patient's mean pulmonary arterial pressure (mPAP) or the patient's altitude of residence.

11. The method of claim 9, wherein introducing the additional amount of diffusion-resistant fluid into the balloon comprises introducing a percentage of the diffusion-resistant fluid of the difference between the desired active volume of fluids within the balloon and the current volume of fluids within the balloon, the percentage of the diffusion-resistant fluid selected to cause an influx of the one or more constituent fluids into the balloon to achieve the desired active volume of fluids within the balloon over time.

12. The method of claim 11, wherein the additional amount of diffusion-resistant fluid comprises 10-25% of the difference between the desired active volume of fluids within the balloon and the current volume of fluids within the balloon.

13. The method of claim 11, further comprising permitting the one or more constituent fluids to equilibrate across the balloon such that each of the one or more constituent fluids is pressurized within the balloon to match their respective partial pressure in the blood surrounding the balloon within the blood vessel to thereby achieve the desired active volume of fluids within the balloon.

14. The method of claim 9, wherein introducing the additional amount of diffusion-resistant fluid into the balloon comprises introducing a fluid mixture volume into the balloon equal to the difference between the desired active volume of fluids within the balloon and the current volume of fluids within the balloon, the fluid mixture volume comprising one or more constituent fluids and a percentage of the diffusion-resistant fluid selected based on at least one of the patient's mean pulmonary arterial pressure (mPAP) or the patient's altitude of residence.

15. The method of claim 14, wherein introducing the fluid mixture volume into the balloon comprises introducing the fluid mixture to reach a predetermined state within the balloon based on at least one of sensed parameters of the patient's physiology or sensed parameters within the balloon.

16. The method of claim 15, wherein the predetermined state comprises at least one of reservoir pulse pressure peak, reservoir pulse pressure decline, or diastolic pressure increase rate exceeding a predetermined threshold.

17. A method for refilling an implantable system, the method comprising:

determining a current volume of fluids within a balloon implanted within a blood vessel of a patient, the current volume of fluids comprising one or more constituent fluids and a diffusion-resistant fluid, each of the one or more constituent fluids pressurized within the balloon to match their respective partial pressure in the blood surrounding the balloon within the blood vessel;

determining a desired active volume of fluids within the balloon; and extracting fluids from the balloon or introducing an additional amount of diffusion-resistant fluid into the balloon to achieve the desired active volume of fluids within the balloon based on the current volume of fluids within the balloon, wherein the diffusion-resistant fluid and the one or more constituent fluids within the balloon are pressurized such that the balloon is transitionable between an expanded state and a collapsed state responsive to pressure fluctuations in the blood vessel.

18. The method of claim 17, wherein achieving the desired active volume of fluids within the balloon comprises extracting fluids from the balloon if the current volume of fluids within the balloon is greater than the desired active volume of fluids within the balloon.

19. The method of claim 17, wherein achieving the desired active volume of fluids within the balloon comprises introducing the additional amount of diffusion-resistant fluid into the balloon if the current volume of fluids within the balloon is less than the desired active volume of fluids within the balloon, and wherein introducing the additional amount of diffusion-resistant fluid into the balloon comprises introducing a percentage of the diffusion-resistant fluid of the difference between the desired active volume of fluids within the balloon and the current volume of fluids within the balloon, the percentage of the diffusion-resistant fluid selected to cause an influx of the one or more constituent fluids into the balloon to achieve the desired active volume of fluids within the balloon over time.

20. The method of claim 17, wherein achieving the desired active volume of fluids within the balloon comprises introducing the additional amount of diffusion-resistant fluid into the balloon if the current volume of fluids within the balloon is less than the desired active volume of fluids within the balloon, and wherein introducing the additional amount of diffusion-resistant fluid into the balloon comprises introducing a fluid mixture volume into the balloon equal to the difference between the desired active volume of fluids within the balloon and the current volume of fluids within the balloon, the fluid mixture volume comprising one or more constituent fluids and a percentage of the diffusion-resistant fluid selected based on at least one of the patient's mean pulmonary arterial pressure (mPAP) or the patient's altitude of residence.

* * * * *